(12) United States Patent
Danishefsky et al.

(10) Patent No.: US 7,635,750 B2
(45) Date of Patent: Dec. 22, 2009

(54) METHOD FOR PREPARING POLYFUNCTIONALIZED PEPTIDES AND/OR PROTEINS VIA NATIVE CHEMICAL LIGATION

(75) Inventors: Samuel J. Danishefsky, Englewood, NJ (US); J. David Warren, New York, NY (US)

(73) Assignee: Sloan-Kettering Institute For Cancer Research, New York, NY (US)

( * ) Notice: Subject to any disclaimer, the term of this patent is extended or adjusted under 35 U.S.C. 154(b) by 123 days.

(21) Appl. No.: 10/570,556

(22) PCT Filed: Sep. 3, 2004

(86) PCT No.: PCT/US2004/029047

§ 371 (c)(1),
(2), (4) Date: Sep. 29, 2006

(87) PCT Pub. No.: WO2005/044841

PCT Pub. Date: May 19, 2005

(65) Prior Publication Data

US 2007/0173636 A1    Jul. 26, 2007

Related U.S. Application Data

(60) Provisional application No. 60/500,708, filed on Sep. 5, 2003, provisional application No. 60/560,147, filed on Apr. 7, 2004.

(51) Int. Cl.
    *C07K 9/00*      (2006.01)
    *A01N 37/18*      (2006.01)
    *A61K 38/14*      (2006.01)

(52) U.S. Cl. .............................. 530/322; 514/2; 514/8; 514/23; 514/25

(58) Field of Classification Search ........................ None
See application file for complete search history.

(56) References Cited

U.S. PATENT DOCUMENTS

| | | |
|---|---|---|
| 6,660,714 B1 | 12/2003 | Danishefsky et al. |
| 2003/0038453 A1 | 2/2003 | Seksaria et al. |
| 2003/0038471 A1 | 2/2003 | Svartz et al. |
| 2003/0153492 A1 | 8/2003 | Danishefsky et al. |
| 2004/0208884 A1 | 10/2004 | Danishefsky et al. |

FOREIGN PATENT DOCUMENTS

| | | |
|---|---|---|
| WO | WO-9634878 | 11/1996 |
| WO | WO-0219963 | 3/2002 |

OTHER PUBLICATIONS

TF listing from NCBI, pp. 1-3. Accessed Sep. 10, 2008.*
N3 listing from NCBI, pp. 1-3. Accessed Sep. 10, 2008.*
Definition of Moiety, from www.dictionary.com, pp. 1-3, Accessed Jan. 29, 2009.*
Arsequell, et al., Tetrahedron Asymmetry, 10: 3045-3094, 1999.
Berman, et al., Nucleic Acids Res., 28: 235-242, 2000.
Bertozzi, et al., Science, 291: 2357-2364, 2001.
Bezay, et al., J. Angew. Chem. Int. Ed., 40: 2292-2295, 2001.
Blixt, et al., J. Am. Chem. Soc., 124: 5739-5746, 2002.
Brask, et al., Org. Lett., 5: 2951-2953, 2003.
Bu, et al., Tetrahedron Lett., 43: 2419-2422, 2002.
Calarese, et al., Science, 300: 2065-2071, 2003.
Cane, et al., Tetrahedron Lett., 36: 1217-1220, 1995.
Caserio, et al., J. Org. Chem., 50: 4390-4393, 1985.
Cheetham, et al., Nat. Struct. Biol., 5: 861-866, 1998.
Chen, et al., J. Am. Chem. Soc., 120: 7760-7769, 1998.
Chiesa, et al., Eur. J. Org. Chem., 3541-3554, 2000.
Ciommer, et al., Synlett, 593-595, 1991.
Clippingdale, et al., J. Pept. Sci., 6: 225-234, 2000.
Cohen-Anisfeld, et al., J. Am. Chem. Soc., 115: 10531-10537, 1993.
Cohen-Anisfeld, et al., J. Org. Chem., 55: 5560-5562, 1990.
Dawson, et al., Science, 266: 776-779, 1994.
Dawson, et al., Annu. Rev. Biochem., 69: 923, 2000.
Dudkin, et al., J. Am. Chem. Soc., 126: 736-738, 2004.
Durand, et al., Olin. Chem., 46: 795-805, 2000.
Geyer, et al., J. Biol. Chem., 263: 11760-11767, 1988.
Grogan, et al., Annu. Rev. Biochem., 71: 593, 2002.

(Continued)

*Primary Examiner*—Cecilia Tsang
*Assistant Examiner*—Julie Ha
(74) *Attorney, Agent, or Firm*—Choate, Hall & Stewart LLP; Brenda Herschbach Jarrell; John P. Rearick

(57) ABSTRACT

The present invention provides a method for preparing polyfunctionalized peptides and/or proteins at non-adjacent designated sites via native chemical ligation. In certain embodiments, the inventive method is a method for preparing a polyfunctionalized peptide comprising a peptidic backbone made up of four or more amino acids, wherein two or more non-adjacent amino acids are independently subsituted with a moiety having the structure: wherein A and $L^1$ are as defined herein. In certain other embodiments, the inventive method allows the preparation of polyfunctionalized peptides having the general structure: wherein A, $R^{P0}$, $R^{P1}$, $P^{X1}$, $R^{X2}$, $L^1$, to, s, t and q are as defined herein.

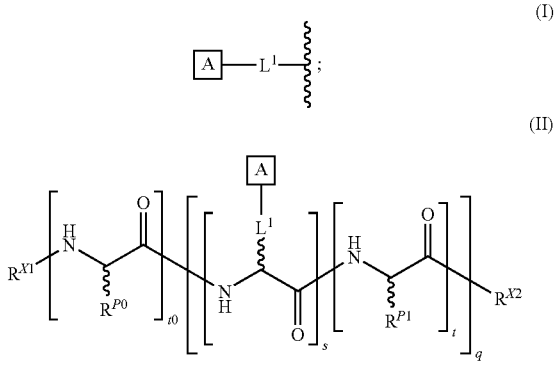

36 Claims, 2 Drawing Sheets

OTHER PUBLICATIONS

Hackeng, et al., PNAS, 96: 10068-10073, 1999.
Hojo, et al., Bull. Chem. Soc. Jpn., 64: 111-117, 1991.
Hojo, et al., Tetrahedron Lett., 44: 2961-2964, 2003.
Imperiali, et al., Pure Appl. Chem., 71: 777-787, 1999.
Ingenito, et al., J. Am. Chem., 121:11369-11374, 1999.
International Preliminary Report on Patentability, PCT/ US04/ 029047, date of mailing on Sep. 3, 2004.
International Search Report, PCT/ US04/029047, date of mailing on Sep. 3, 2004.
Kemp, The Peptides: Analysis, Synthesis, Biology, Academic Press: NY, 1979, vol. 1, Part A: 315-381.
Koeller, et al., J. Am. Chem. Soc., 122: 4241-4242, 2000.
Koeller, et al., Nat. Biotechnol., 18: 835-841, 2000.
Kornfeld, et al., Annu. Rev. Biochem., 54: 631-664, 1985.
Lai, et al., J. Biol. Chem., 261: 3116-3121, 1986.
Li, et al., Tetrahedron Lett., 39: 8669-8672, 1998.
Likhosherstov, et al., Carbohydr. Res., 146: C1-C5, 1986.
Lis, et al., Eur. J. Biochem., 218: 1-27, 1993.
Liu, et al., PNAS, 91: 6584-6588, 1994.
Macmillan, et al., Tetrahedron, 56: 9515-9525, 2000.
Marcaurelle, et al., Glycobiology, 12: 69R-77R, 2002.
Meinjohanns, et al., J. Am. Chem. Soc.-Perkin Trans., 1: 549-560, 1998.
Meinjohanns, et al., Tetrahedron Lett., 36: 9205-9208, 1995.
Miller, et al., J. Angew. Chem. Int. Ed., 42: 431-434, 2003.
Mizuno, et al., J. Am. Chem. Soc., 121: 284-290, 1999.
Muir, et al., PNAS, 95: 6705-6710, 1998.
Peracaula, et al., Glycobiology, 13: 457-470, 2003.
Rahbek-Nielsen, et al., J. Mass Spectrum, 32: 948-958, 1997.
Ridley, et al., J. Nat. Med. Assoc., 86: 129-135, 1994.
Roth, et al., J. Chem. Rev., 102: 285-303, 2002.
Rudd, et al., Science, 291: 2370-2376, 2001.
Rush, et al., Anal. Chem., 67: 1442-1452, 1995.
Shaltiel, et al., Biochem., 9: 5122-5127, 1970.
Shin, et al., J. Am. Chem., 121: 11684-11689, 1999.
Swinnen, et al., Org. Lett., 2: 2439-2442, 2000.
Tolbert, et al., J. Am. Chem. Soc., 122: 5421-5428, 2000.
Unverzagt, Tetrahedron Lett., 38: 5627-5630, 1997.
Van Ameijde, et al., J. Chem. Soc.-Perkin Trans., 1: 1042-1049, 2002.
Verhaeghe, et al., Tetrahedron Lett., 34: 461-464, 1993.
Von Eggelkraut-Gottanka, et al., Tetrahedron Lett., 44: 3551-3554, 2003.
Von Mensdorff-Pouilly, et al., Int. J. Biol. Markers, 15: 343-356, 2000.
Wang, et al., J. Am. Chem. Soc., 119: 11137-11146, 1997.
Wang, et al., J. Angew. Chem. Int. Ed., 39: 3652-3656, 2000.
Witte, et al., J. Am. Chem. Soc., 119: 2114-2118, 1997.
Written Opinion of International Searching Authority, PCT/ US04/ 029047, date of mailing on Sep. 3, 2004.
Zhang, et al., Science, 303: 371-373, 2004.

* cited by examiner (SEQ ID NO: 6)

SEQUENCE LISTING

```
<160> NUMBER OF SEQ ID NOS: 8

<210> SEQ ID NO 1
<211> LENGTH: 5
<212> TYPE: PRT
<213> ORGANISM: Artificial Sequence
<220> FEATURE:
<223> OTHER INFORMATION: Chemical ligation precursor

<400> SEQUENCE: 1

Arg Asp Arg Ser Gly
1               5

<210> SEQ ID NO 2
<211> LENGTH: 6
<212> TYPE: PRT
<213> ORGANISM: Artificial Sequence
```

```
<220> FEATURE:
<223> OTHER INFORMATION: Chemical ligation precursor

<400> SEQUENCE: 2

Arg Asp Arg Ser Gly Phe
1               5

<210> SEQ ID NO 3
<211> LENGTH: 6
<212> TYPE: PRT
<213> ORGANISM: Artificial Sequence
<220> FEATURE:
<223> OTHER INFORMATION: Chemical ligation precursor

<400> SEQUENCE: 3

Arg Asn Arg Ser Gly Phe
1               5

<210> SEQ ID NO 4
<211> LENGTH: 5
<212> TYPE: PRT
<213> ORGANISM: Artificial Sequence
<220> FEATURE:
<223> OTHER INFORMATION: Chemical ligation precursor

<400> SEQUENCE: 4

Cys Ala Asp Ala Ser
1               5

<210> SEQ ID NO 5
<211> LENGTH: 5
<212> TYPE: PRT
<213> ORGANISM: Artificial Sequence
<220> FEATURE:
<223> OTHER INFORMATION: Chemical ligation precursor

<400> SEQUENCE: 5

Cys Ala Asn Ala Ser
1               5

<210> SEQ ID NO 6
<211> LENGTH: 11
<212> TYPE: PRT
<213> ORGANISM: Artificial Sequence
<220> FEATURE:
<223> OTHER INFORMATION: Chemical ligation product

<400> SEQUENCE: 6

Arg Asn Arg Ser Gly Phe Cys Ala Asn Ala Ser
1               5                   10

<210> SEQ ID NO 7
<211> LENGTH: 11
<212> TYPE: PRT
<213> ORGANISM: Artificial Sequence
<220> FEATURE:
<223> OTHER INFORMATION: Chemical ligation product

<400> SEQUENCE: 7

Arg Ala Arg Ser Gly Phe Cys Ala Asn Val Ser
1               5                   10

<210> SEQ ID NO 8
<211> LENGTH: 11
<212> TYPE: PRT
<213> ORGANISM: Artificial Sequence
<220> FEATURE:
```

```
<223> OTHER INFORMATION: Chemical ligation product

<400> SEQUENCE: 8

Arg Asn Arg Ser Gly His Cys Ala Ser Ala Ser
1               5                   10
```

METHOD FOR PREPARING POLYFUNCTIONALIZED PEPTIDES AND/OR PROTEINS VIA NATIVE CHEMICAL LIGATION

PRIORITY CLAIM

This application claims the benefit under 35 U.S.C. § 371 of International Application No.: PCT/US2004/029047 (published PCT application No. WO 2005/044841 A1), filed Sep. 3, 2004, which claims priority to U.S. Patent Application Nos. 60/500,708, filed Sep. 5, 2003; and 60/560,147, filed Apr. 7, 2004; each of the above-cited Applications is hereby incorporated herein by reference in its entirety.

GOVERNMENT SUPPORT

The invention was made with U.S. government support under grants CA103823 (formerly AI16943), T32-CA62948, and AI051883 awarded by the National Institutes of Health. The U.S. government has certain rights in this invention.

BACKGROUND OF THE INVENTION

Glycoproteins are important biomacromolecules that are biosynthesized through posttranslational glycosylation of newly fashioned proteins emerging from the ribosome. Interest in glycoproteins arises at many levels. A long-term goal of the growing field of chemistry-based glycobiology is the delineation of the consequences of glycosylation on critical properties such as protein folding, proteolytic stability, and cell adhesion.[1] Such insights could explain why nature bothers to glycosylate otherwise functional proteins. Moreover, glycoproteins have potentially important clinical roles in the context of vaccines, diagnostics, and therapeutics. Indeed, erythropoietin, albeit a heterogeneous glycoprotein,[5] is clinically valuable as a treatment for anemia, among other indications.[4a]

Many naturally occurring, medicinally important glycoproteins (cf., for example, erythropoietin[4a] and gp120[11]) display multiple glycosylation sites containing large oligosaccharide domains. However, given the complexity and variability of biological glycosylation pathways,[10] the isolation of homogeneous glycoproteins from natural sources in significant quantity is extremely difficult.

Numerous methods exist for the production of glycopeptides by chemical synthesis. For example, glycans have been introduced into peptides via amino acid "cassettes" with pendant protected saccharides,[26-31] through enzymatic manipulations of glycopeptides,[32-38] or by conjugation of fully elaborated, complex saccharides to short synthetic peptides.[39-41] Larger O-linked glycopeptides have been synthesized using ligation techniques[42-43] such as expressed protein ligation.[44-46] Bertozzi and coworkers extended the scope of the "cassette" approach by applying native chemical ligation to the synthesis of a biologically active glycoprotein with two single-residue O-linked glycans.[47] Tolbert and Wong described the ligation of a 392-residue intein-generated peptide thioester and a dipeptide functionalized with a single N-acetylglucosamine residue. However, none of these approaches has allowed the assembly of complex glypeptides or glycoproteins multiply functionalized (e.g., multiply glycosylated) at designated sites.

Accordingly, there remains a need for novel synthetic methods leading to the preparation of homogeneous polyfunctionalized peptides and/or proteins. Specifically, convergent, stereoselective, versatile methods for preparing such glycopeptides and/or glycoproteins are needed.

SUMMARY OF THE INVENTION

In recognition of the need to provide access to polyfunctionalized peptides and proteins, the present invention, in one aspect, provides a system for preparing a polyfunctionalized peptide comprising a peptidic backbone made up of four or more amino acids, wherein two or more non-adjacent amino acids are independently substituted with a moiety having the structure:

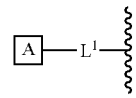

with the proviso that the peptide sequence between any two consecutive, non-adjacent, amino acids bearing a A-L$^1$- moiety comprises at least one cysteine residue;

wherein the method comprises a step of:

reacting a peptide acyl donor comprising a peptidic backbone made up of two or more amino acids wherein said peptide acyl donor has the structure:

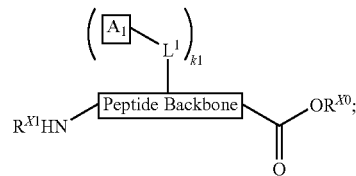

with a peptide amine acceptor having the structure:

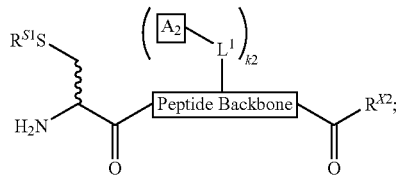

under suitable conditions to effect ligation;

wherein k1 and k2 are independently integers between 1 and about 20;

each occurrence of A, A$_1$ and A$_2$ is independently an aliphatic, heteroaliphatic, aromatic, heteroaromatic, aryl, heteroaryl or a pharmaceutically useful group or entity;

R$^{S1}$ is a sulfide protecting group;

R$^{X0}$ is a group such that the moiety —C(=O)OR$^{X0}$ can be made to undergo ligation with the peptide amine acceptor;

each occurrence of L$^1$ is independently a substituted or unsubstituted, linear or branched, cyclic or acyclic, saturated or unsaturated aliphatic or heteroaliphatic moiety;

R$^{X1}$ is hydrogen, alkyl, acyl, aromatic, heteroaromatic, aryl, heteroaryl, -alkyl(aryl), -alkyl(heteroaryl), a nitrogen protecting group, an amino acid or a proctected amino acid;

R$^{X2}$ is —OR$^{X2a}$ or —NR$^{X2b}$R$^{X2c}$, wherein R$^{X2a}$ is hydrogen, alkyl, aromatic, aryl, heteroaryl, -alkyl(aryl), -alkyl(heteroaryl), a carboxylic acid protecting group, an amino acid or a proctected amino acid; and $R^{X2b}$ and $R^{X2c}$ are independently hydrogen, alkyl, aromatic, heteroaromatic, aryl, heteroaryl, -alkyl(aryl), -alkyl(heteroaryl), a nitrogen protecting group, an amino acid or a proctected amino acid.

In certain embodiments, each occurrence of A is independently a pharmaceutically useful group or entity. In certain embodiments, each occurrence of A is independently a biomolecule, a small molecule, a macromolecule or a diagnostic label.

In certain exemplary embodiments, each occurrence of A is independently a carbohydrate determinant having the structure:

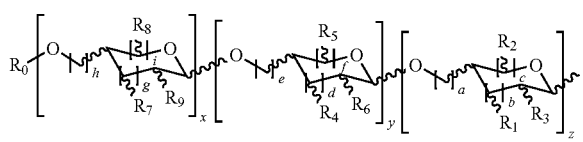

1 or 2, and the sum of s and u is 1 or 2, and with the proviso that v and w are not simultaneously 0; wherein $R'_0$ is hydrogen, a linear or branched chain alkyl, acyl, arylalkyl or aryl group; wherein each occurrence of $R_{10}$, $R_{11}$, $R_{12}$, $R_{13}$, $R_{14}$ and $R_{15}$ is independently hydrogen, OH, $OR^{iii}$, $NHR^{iii}$, $NHCOR^{iii}$, F, $CH_2OH$, $CH_2OR^{iii}$, or a substituted or unsubstituted linear or branched chain alkyl, (mono-, di- or tri)hydroxyalkyl, (mono-, di- or tri)acyloxyalkyl, arylalkyl or aryl group; wherein each occurrence of $R_{16}$ is hydrogen, COOH, $COOR^{ii}$, $CONHR^{ii}$, a substituted or unsubstituted linear or branched chain alkyl or aryl group; wherein each occurrence of $R^{iii}$ is hydrogen, CHO, $COOR^{iv}$, or a substituted or unsubstituted linear or branched chain alkyl, acyl, arylalkyl or aryl group; and wherein each occurrence of $R^{ii}$ and $R^{iv}$ are each independently H, or a substituted or unsubstituted linear or branched chain alkyl, arylalkyl or aryl group.

In certain embodiments, the present invention provides a method for preparing a polyfunctionalized peptide having the structure:

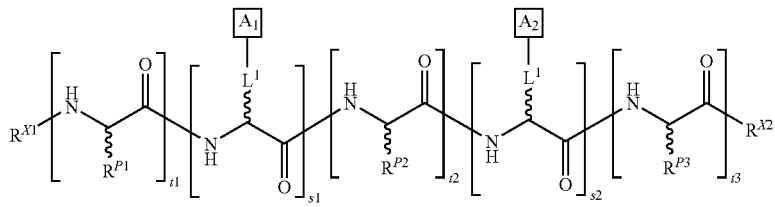

wherein a, b, c, d, e, f, g, h, i, x, y and z are independently 0, 1, 2 or 3, with the proviso that the x, y and z bracketed structures represent furanose or pyranose moieties and the sum of b and c is 1 or 2, the sum of d and f is 1 or 2, and the sum of g and i is 1 or 2, and with the proviso that x, y and z are not simultaneously 0; wherein $R_0$ is hydrogen, a linear or branched chain alkyl, acyl, arylalkyl or aryl group; wherein each occurrence of $R_1$, $R_2$, $R_3$, $R_4$, $R_5$, $R_6$, $R_7$, $R_8$ and $R_9$ is independently hydrogen, OH, $OR^i$, $NHR^i$, $NHCOR^i$, F, $CH_2OH$, $CH_2OR^i$, a substituted or unsubstituted linear or branched chain alkyl, (mono-, di- or tri)hydroxyalkyl, (mono-, di- or tri)acyloxyalkyl, arylalkyl or aryl group; wherein each occurrence of $R^i$ is independently hydrogen, CHO, $COOR^{ii}$, or a substituted or unsubstituted linear or branched chain alkyl, acyl, arylalkyl or aryl group or a saccharide moiety having the structure:

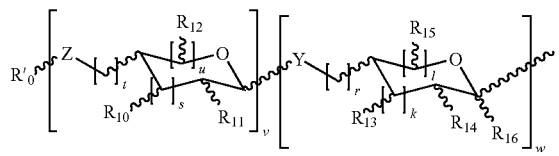

wherein Y and Z are independently NH or O; wherein k, l, r, s, t, u, v and w are each independently 0, 1 or 2; with the proviso that the v and w bracketed structures represent furanose or pyranose moieties and the sum of l and k is wherein s1 and s2 are independently an integer from 1 to about 20;

t1, t2 and t3 are each independently an integer;

$R^{X1}$ is hydrogen, alkyl, acyl, aromatic, heteroaromatic, aryl, heteroaryl, -alkyl(aryl), -alkyl(heteroaryl), a nitrogen protecting group, an amino acid or a proctected amino acid;

$R^{X2}$ is —O $R^{X2a}$ or —$NR^{X2b}R^{X2c}$, wherein $R^{X2a}$ is hydrogen, alkyl, aromatic, heteroaromatic, aryl, heteroaryl, -alkyl(aryl), -alkyl(heteroaryl), a carboxylic acid protecting group, an amino acid or a proctected amino acid; and $R^{X2b}$ and $R^{X2c}$ are independently hydrogen, alkyl, aromatic, heteroaromatic, aryl, heteroaryl, -alkyl(aryl), -alkyl(heteroaryl), a nitrogen protecting group, an amino acid or a proctected amino acid;

$R^{P1}$, $R^{P2}$ and $R^{P3}$ are independently H, alkyl, heteroalkyl, aromatic, heteroaromatic, aryl, heteroaryl, -alkyl(aryl), -akyl(heteroaryl), or a natural or non-natural amino acid side chain;

each occurrence of $L^1$ is independently a substituted or unsubstituted aliphatic or heteroaliphatic moiety;

$A_1$ and $A_2$ are each independently an aliphatic, heteroaliphatic, aromatic, heteroaromatic, aryl, heteroaryl or a pharmaceutically useful group or entity; and at least one occurrence of the bracketed structure t2 is a cysteine residue or protected cysteine residue;

wherein the method comprise a step of:
reacting a peptide acyl donor having the structure:

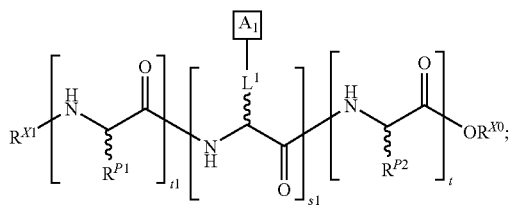

with a peptide amine acceptor having the structure:

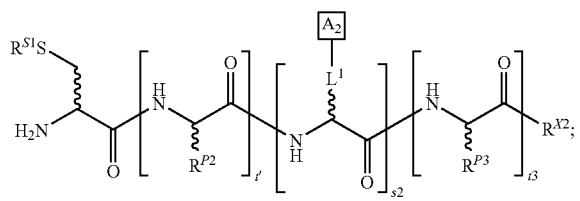

under suitable conditions to effect ligation;
wherein the sum t+t' equals (t2)+1; $R^{S1}$ is a sulfide protecting group; and $R^{X0}$ is a group such that the moiety —C(=O)$OR^{X0}$ can be made to undergo ligation with the glycopeptide amine acceptor.

In certain exemplary embodiments, $A_1$ and $A_2$ are each independently a carbohydrate domain as defined for A above.

In certain embodiments, the step may be carried out once, or repeated a desired number of times, to prepare the polyfunctionalized peptide having the structure:

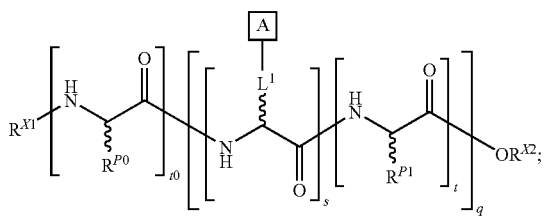

wherein $R^{X1}$ and $R^{X2}$ are as defined above;
each occurrence of A may be the same or different and may be as defined for $A_1$ and $A_2$ above;
each occurrence of $R^{P1}$ may be the same or different and may be as defined for $R^{P1}$ and $R^{P2}$ above;
q is an integer greater than or equal to 2;
each occurrence of s is independently an integer from 1 to about 20;
each occurrence of t is independently an integer;
t0 is an integer; and
each occurrence of $R^{P0}$ is independently H, alkyl, heteroalkyl, aromatic, heteroaromatic, aryl, heteroaryl -alkyl(aryl), -alkylheteroaryl), or a natural or non-natural amino acid side chain.

Definitions

Certain specific functional groups defined in the inventive method are described in more detail below. For purposes of this invention, the chemical elements are identified in accordance with the Periodic Table of the Elements, CAS version, Handbook of Chemistry and Physics, 75$^{th}$ Ed., inside cover, and specific functional groups are defined as described therein. Additionally, general principles of organic chemistry, as well as specific functional moieties and reactivity, are described in "Organic Chemistry", Thomas Sorrell, University Science Books, Sausalito: 1999, the entire contents of which are incorporated herein by reference.

It will be appreciated that the compounds, as described herein, may be substituted with any number of substituents or functional moieties. In general, the term "substituted" whether preceded by the term "optionally" or not, and substituents contained in formulas of this invention, refer to the replacement of hydrogen radicals in a given structure with the radical of a specified substituent. When more than one position in any given structure may be substituted with more than one substituent selected from a specified group, the substituent may be either the same or different at every position. As used herein, the term "substituted" is contemplated to include all permissible substituents of organic compounds. In a broad aspect, the permissible substituents include acyclic and cyclic, branched and unbranched, carbocyclic and heterocyclic, aromatic and non-aromatic, carbon and heteroatom substituents of organic compounds. For purposes of this invention, heteroatoms such as nitrogen may have hydrogen substituents and/or any permissible substituents of organic compounds described herein which satisfy the valencies of the heteroatoms. Furthermore, this invention is not intended to be limited in any manner by the permissible substituents of organic compounds. Combinations of substituents and variables envisioned by this invention are preferably those that result in the formation of stable compounds useful in the treatment and prevention, for example of disorders, as described generally above. Examples of substituents include, but are not limited to aliphatic; heteroaliphatic; alicyclic; heteroalicyclic; aromatic, heteroaromatic; aryl; heteroaryl; alkylaryl; alkylheteroaryl; alkoxy; aryloxy; heteroalkoxy; heteroaryloxy; alkylthio; arylthio; heteroalkylthio; heteroarylthio; F; Cl; Br; I; —NO$_2$; —CN; —CF$_3$; —CH$_2$CF$_3$; —CHCl$_2$; —CH$_2$OH; —CH$_2$CH$_2$OH; —CH$_2$NH$_2$; —CH$_2$SO$_2$CH$_3$; — or —GR$^{G1}$ wherein G is —O—, —S—, —NR$^{G2}$—, —C(=O)—, —S(=O)—, —SO$_2$—, —C(=O)O—, —C(=O)NR$^{G2}$—, —OC(=O)—, —NR$^{G2}$C(=O)—, —OC(=O)O—, —OC(=O)NR$^{G2}$—, —NR$^{G2}$C(=O)O—, —NR$^{G2}$C(=O)NR$^{G2}$—, —C(=S)—, —C(=S)S—, —SC(=S)—, —SC(=S)S—, —C(=NR$^{G2}$)—, —C(=NR$^{G2}$)O—, —C(=NR$^{G2}$)NR$^{G3}$, —OC(=NR$^{G2}$)—, —NR$^{G2}$C(=NR$^{G3}$)—, —NR$^{G2}$SO$_2$—, —NR$^{G2}$SO$_2$NR$^{G3}$—, or —SO$_2$NR$^{G2}$—, wherein each occurrence of R$^{G1}$, R$^{G2}$ and R$^{G3}$ independently includes, but is not limited to, hydrogen, halogen, or an optionally substituted aliphatic, heteroaliphatic, alicyclic, heteroalicyclic, aromatic, heteroaromatic, aryl, heteroaryl, alkylaryl, or alkylheteroaryl moiety. Additional examples of generally applicable substituents are illustrated by the specific embodiments shown in the Examples that are described herein.

The term "stable", as used herein, preferably refers to compounds which possess stability sufficient to allow manufacture and which maintain the integrity of the compound for a sufficient period of time to be useful for the purposes detailed herein.

The term "aliphatic", as used herein, includes both saturated and unsaturated, straight chain (i.e., unbranched) or branched aliphatic hydrocarbons, which are optionally substituted with one or more functional groups. As will be appreciated by one of ordinary skill in the art, "aliphatic" is intended herein to include, but is not limited to, alkyl, alkenyl, alkynyl moieties. Thus, as used herein, the term "alkyl" includes straight and branched alkyl groups. An analogous convention applies to other generic terms such as "alkenyl", "alkynyl" and the like. Furthermore, as used herein, the terms "alkyl", "alkenyl", "alkynyl" and the like encompass both substituted and unsubstituted groups. In certain embodiments, as used herein, "lower alkyl" is used to indicate those alkyl groups (substituted, unsubstituted, branched or unbranched) having about 1-6 carbon atoms.

In certain embodiments, the alkyl, alkenyl and alkynyl groups employed in the invention contain about 1-20 aliphatic carbon atoms. In certain other embodiments, the alkyl, alkenyl, and alkynyl groups employed in the invention contain about 1-10 aliphatic carbon atoms. In yet other embodiments, the alkyl, alkenyl, and alkynyl groups employed in the invention contain about 1-8 aliphatic carbon atoms. In still other embodiments, the alkyl, alkenyl, and alkynyl groups employed in the invention contain about 1-6 aliphatic carbon atoms. In yet other embodiments, the alkyl, alkenyl, and alkynyl groups employed in the invention contain about 1-4 carbon atoms. Illustrative aliphatic groups thus include, but are not limited to, for example, methyl, ethyl, n-propyl, isopropyl, allyl, n-butyl, sec-butyl, isobutyl, tert-butyl, n-pentyl, sec-pentyl, isopentyl, tert-pentyl, n-hexyl, sec-hexyl, moieties and the like, which again, may bear one or more substituents. Alkenyl groups include, but are not limited to, for example, ethenyl, propenyl, butenyl, 1-methyl-2-buten-1-yl, and the like. Representative alkynyl groups include, but are not limited to, ethynyl, 2-propynyl (propargyl), 1-propynyl and the like.

The term "alicyclic", as used herein, refers to compounds which combine the properties of aliphatic and cyclic compounds and include but are not limited to cyclic, or polycyclic aliphatic hydrocarbons and bridged cycloalkyl compounds, which are optionally substituted with one or more functional groups. As will be appreciated by one of ordinary skill in the art, "alicyclic" is intended herein to include, but is not limited to, cycloalkyl, cycloalkenyl, and cycloalkynyl moieties, which are optionally substituted with one or more functional groups. Illustrative alicyclic groups thus include, but are not limited to, for example, cyclopropyl, —CH$_2$-cyclopropyl, cyclobutyl, —CH$_2$-cyclobutyl, cyclopentyl, —CH$_2$-cyclopentyl-n, cyclohexyl, —CH$_2$-cyclohexyl, cyclohexenylethyl, cyclohexanylethyl, norborbyl moieties and the like, which again, may bear one or more substituents.

The term "cycloalkyl", as used herein, refers specifically to groups having three to seven, preferably three to ten carbon atoms. Suitable cycloalkyls include, but are not limited to cyclopropyl, cyclobutyl, cyclopentyl, cyclohexyl, cycloheptyl and the like, which, as in the case of aliphatic, heteroaliphatic or heterocyclic moieties, may optionally be substituted. An analogous convention applies to other generic terms such as "cycloalkenyl", "cycloalkynyl" and the like.

The term "heteroaliphatic", as used herein, refers to aliphatic moieties in which one or more carbon atoms in the main chain have been substituted with a heteroatom. Thus, a heteroaliphatic group refers to an aliphatic chain which contains one or more oxygen, sulfur, nitrogen, phosphorus or silicon atoms, e.g., in place of carbon atoms. Heteroaliphatic moieties may be branched or linear unbranched. In certain embodiments, heteroaliphatic moieties are substituted by independent replacement of one or more of the hydrogen atoms thereon with one or more moieties including, but not limited to aliphatic; heteroaliphatic; alicyclic; heteroalicyclic; aromatic, heteroaromatic; aryl; heteroaryl; alkylaryl; alkylheteroaryl; alkoxy; aryloxy; heteroalkoxy; heteroaryloxy; alkylthio; arylthio; heteroalkylthio; heteroarylthio; F; Cl; Br; I; —NO$_2$; —CN; —CF$_3$; —CH$_2$CF$_3$; —CHCl$_2$; —CH$_2$OH; —CH$_2$CH$_2$OH; —CH$_2$NH$_2$; —CH$_2$SO$_2$CH$_3$; — or —GR$^{G1}$ wherein G is —O—, —S—, —NR$^{G2}$—, —C(=O)—, —S(=O)—, —SO$_2$—, —C(=O)O—, —C(=O)NR$^{G2}$—, —OC(=O)—, —NR$^{G2}$C(=O)—, —OC(=O)O—, —OC(=O)NR$^{G2}$—, —NR$^{G2}$C(=O)O—, —NR$^{G2}$C(=O)NR$^{G2}$—, —C(=S)—, —C(=S)S—, —SC(=S)—, —SC(=S)S—, —C(=NR$^{G2}$)—, —C(=NR$^{G2}$)O—, —C(=NR$^{G2}$)NR$^{G3}$—, —OC(=NR$^{G2}$)—, —NR$^{G2}$C(=NR$^{G3}$)—, —NR$^{G2}$SO$_2$—, —NR$^{G2}$SO$_2$NR$^{G3}$—, or —SO$_2$NR$^{G2}$—, wherein each occurrence of R$^{G1}$, R$^{G2}$ and R$^{G3}$ independently includes, but is not limited to, hydrogen, halogen, or an optionally substituted aliphatic, heteroaliphatic, alicyclic, heteroalicyclic, aromatic, heteroaromatic, aryl, heteroaryl, alkylaryl, or alkylheteroaryl moiety. Additional examples of generally applicable substituents are illustrated by the specific embodiments shown in the Examples that are described herein.

The term "heteroalicyclic", "heterocycloalkyl" or "heterocyclic", as used herein, refers to compounds which combine the properties of heteroaliphatic and cyclic compounds and include but are not limited to saturated and unsaturated mono- or polycyclic heterocycles such as morpholino, pyrrolidinyl, furanyl, thiofuranyl, pyrrolyl etc., which are optionally substituted with one or more functional groups, as defined herein. In certain embodiments, the term "heterocyclic" refers to a non-aromatic 5-, 6- or 7-membered ring or a polycyclic group, including, but not limited to a bi- or tri-cyclic group comprising fused six-membered rings having between one and three heteroatoms independently selected from oxygen, sulfur and nitrogen, wherein (i) each 5-membered ring has 0 to 2 double bonds and each 6-membered ring has 0 to 2 double bonds, (ii) the nitrogen and sulfur heteroatoms may optionally be oxidized, (iii) the nitrogen heteroatom may optionally be quaternized, and (iv) any of the above heterocyclic rings may be fused to an aryl or heteroaryl ring. Representative heterocycles include, but are not limited to, pyrrolidinyl, pyrazolinyl, pyrazolidinyl, imidazolinyl, imidazolidinyl, piperidinyl, piperazinyl, oxazolidinyl, isoxazolidinyl, morpholinyl, thiazolidinyl, isothiazolidinyl, and tetrahydrofuryl. In certain embodiments, a "substituted heterocycloalkyl or heterocycle" group is utilized and as used herein, refers to a heterocycloalkyl or heterocycle group, as defined above, substituted by the independent replacement of one, two or three of the hydrogen atoms thereon with but are not limited to aliphatic; heteroaliphatic; alicyclic; heteroalicyclic; aromatic, heteroaromatic; aryl; heteroaryl; alkylaryl; alkylheteroaryl; alkoxy; aryloxy; heteroalkoxy; heteroaryloxy; alkylthio; arylthio; heteroalkylthio; heteroarylthio; F; Cl; Br; I; —NO$_2$; —CN; —CF$_3$; —CH$_2$CF$_3$; —CHCl$_2$; —CH$_2$OH; —CH$_2$CH$_2$OH; —CH$_2$NH$_2$; —CH$_2$SO$_2$CH$_3$; — or —GR$^{G1}$ wherein G is —O—, —S—, —NR$^{G2}$—, —C(=O)—, —S(=O)—, —SO$_2$—, —C(=O)O—, —C(=O)NR$^{G2}$—, —OC(=O)—, —NR$_{G2}$C(=O)—, —OC(=O)O—, —OC(=O)NR$^{G2}$—, —NR$^{G2}$C(=O)O—, —NR$^{G2}$C(=O)NR$^{G2}$, —C(=S)—, —C(=S)S—, —SC(=S)—, —SC(=S)S—, —C(=NR$^{G2}$)—, —C(=NR$^{G2}$)O—, —C(=NR$^{G2}$)NR$^{G3}$—, —OC(=NR$^{G2}$)—, —NR$^{G2}$C(=NR$^{G3}$)—, —NR$^{G2}$SO$_2$—, —NR$^{G2}$SO$_2$NR$^{G3}$—, or —SO$_2$NR$^{G2}$—, wherein each occurrence of R$^{G1}$, R$^{G2}$ and R$^{G3}$ independently includes, but is not limited to, hydrogen, halogen, or an optionally substituted aliphatic, heteroaliphatic, alicyclic, heteroalicyclic, aromatic, heteroaromatic, aryl, heteroaryl, alkylaryl, or alkylheteroaryl moiety. Additional examples or generally applicable substituents are illustrated by the specific embodiments shown in the Examples, which are described herein.

Additionally, it will be appreciated that any of the alicyclic or heteroalicyclic moieties described above and herein may comprise an aryl or heteroaryl moiety fused thereto. Additional examples of generally applicable substituents are illustrated by the specific embodiments shown in the Examples that are described herein.

In general, the term "aromatic moiety", as used herein, refers to stable substituted or unsubstituted unsaturated mono- or polycyclic hydrocarbon moieties having preferably 3-14 carbon atoms, comprising at least one ring satisfying the Huckel rule for aromaticity. Examples of aromatic moieties include, but are not limited to, phenyl, indanyl, indenyl, naphthyl, phenanthryl and anthracyl.

In general, the term "heteroaromatic moiety", as used herein, refers to stable substituted or unsubstituted unsaturated mono-heterocyclic or polyheterocyclic moieties having preferably 3-14 carbon atoms, comprising at least one ring satisfying the Huckel rule for aromaticity. Examples of heteroaromatic moieties include, but are not limited to, pyridyl, quinolinyl, dihydroquinolinyl, isoquinolinyl, quinazolinyl, dihydroquinazolyl, and tetrahydroquinazolyl.

It will also be appreciated that aromatic and heteroaromatic moieties, as defined herein, may be attached via an aliphatic (e.g., alkyl) or heteroaliphatic (e.g., heteroalkyl) moiety and thus also include moieties such as -(aliphatic)aromatic, -(heteroaliphatic)aromatic, -(aliphatic)heteroaromatic, -(heteroaliphatic)heteroaromatic, (alkyl)aromatic, -(heteroalkyl)aromatic, -(alkyl)heteroaromatic, and -(heteroalkyl)heteroaromatic moieties. Thus, as used herein, the phrases "aromatic or heteroaromatic moieties" and "aromatic, heteroaromatic, -(alkyl)aromatic, -(heteroalkyl)aromatic, -(heteroalkyl)heteroaromatic, and (heteroalkyl)heteroaromatic" are interchangeable. Substituents include, but are not limited to, any of the previously mentioned substituents, i.e., the substituents recited for aliphatic moieties, or for other moieties as disclosed herein, resulting in the formation of a stable compound.

In general, the term "aryl" refers to aromatic moieties, as described above, excluding those attached via an aliphatic (e.g., alkyl) or heteroaliphatic (e.g., heteroalkyl) moiety. In certain embodiments of the present invention, "aryl" refers to a mono- or bicyclic carbocyclic ring system having one or two rings satisfying the Huckel rule for aromaticity, including, but not limited to, phenyl, naphthyl, tetrahydronaphthyl, indanyl, indenyl and the like.

Similarly, the term "heteroaryl" refers to heteroaromatic moieties, as described above, excluding those attached via an aliphatic (e.g., alkyl) or heteroaliphatic (e.g., heteroalkyl) moiety. In certain embodiments of the present invention, the term "heteroaryl", as used herein, refers to a cyclic unsaturated radical having from about five to about ten ring atoms of which one ring atom is selected from S, O and N; zero, one or two ring atoms are additional heteroatoms independently selected from S, O and N; and the remaining ring atoms are carbon, the radical being joined to the rest of the molecule via any of the ring atoms, such as, for example, pyridyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, and the like.

Substituents for aryl and heteroaryl moieties include, but are not limited to, any of the previously mentioned substitutents, i.e., the substituents recited for aliphatic moieties, or for other moieties as disclosed herein, resulting in the formation of a stable compound. For example, aryl and heteroaryl groups (including bicyclic aryl groups) can be unsubstituted or substituted, wherein substitution includes replacement of one, two or three of the hydrogen atoms thereon independently with any one or more of the following moieties including, but not limited to: aliphatic; heteroaliphatic; alicyclic; heteroalicyclic; aromatic, heteroaromatic; aryl; heteroaryl; alkylaryl; alkylheteroaryl; alkoxy; aryloxy; heteroalkoxy; heteroaryloxy; alkylthio; arylthio; heteroalkylthio; heteroarylthio; F; Cl; Br; I; —$NO_2$; —CN; —$CF_3$; —$CH_2CF_3$; —$CHCl_2$; —$CH_2OH$; —$CH_2CH_2OH$; —$CH_2NH_2$; —$CH_2SO_2CH_3$; — or —$GR^{G1}$ wherein G is —O—, —S—, —$NR^{G2}$—, —C(=O)—, —S(=O)—, —$SO_2$—, —C(=O)O—, —C(=O)$NR^{G2}$—, —OC(=O)—, —$NR^{G2}$C(=O)—, —OC(=O)O—, —OC(=O)$NR^{G2}$—, —$NR^{G2}$C(=O)O—, —$NR^{G2}$C(=O)$NR^{G2}$—, —C(=S)—, —C(=S)S—, —SC(=S)—, —SC(=S)S—, —C(=$NR^{G2}$)—, —C(=$NR^{G2}$)O—, —C(=$NR^{G2}$)$NR^{G3}$—, —OC(=$NR^{G2}$)—, $NR^{G2}$C(=$NR^{G3}$)—, —$NR^{G2}SO_2$—, —$NR^{G2}SO_2NR^{G3}$—, or —$SO_2NR^{G2}$—, wherein each occurrence of $R^{G1}$, $R^{G2}$ and $R^{G3}$ independently includes, but is not limited to, hydrogen, halogen, or an optionally substituted aliphatic, heteroaliphatic, alicyclic, heteroalicyclic, aromatic, heteroaromatic, aryl, heteroaryl, alkylaryl, or alkylheteroaryl moiety. Additional examples of generally applicable substituents are illustrated by the specific embodiments shown in the Examples that are described herein.

The terms "alkoxy" (or "alkyloxy"), and "thioalkyl" as used herein refers to an alkyl group, as previously defined, attached to the parent molecular moiety through an oxygen atom ("alkoxy") or through a sulfur atom ("thioalkyl"). In certain embodiments, the alkyl group contains about 1-20 aliphatic carbon atoms. In certain other embodiments, the alkyl group contains about 1-10 aliphatic carbon atoms. In yet other embodiments, the alkyl group contains about 1-8 aliphatic carbon atoms. In still other embodiments, the alkyl group contains about 1-6 aliphatic carbon atoms. In yet other embodiments, the alkyl group contains about 1-4 aliphatic carbon atoms. Examples of alkoxy groups, include but are not limited to, methoxy, ethoxy, propoxy, isopropoxy, n-butoxy, tert-butoxy, neopentoxy and n-hexoxy. Examples of thioalkyl groups include, but are not limited to, methylthio, ethylthio, propylthio, isopropylthio, n-butylthio, and the like.

The term "amine" refers to a group having the structure —$N(R)_2$ wherein each occurrence of R is independently hydrogen, or an aliphatic, heteroaliphatic, aromatic or heteroaromatic moiety, or the R groups, taken together, may form a heterocyclic moiety.

The term "alkylamino" refers to a group having the structure —NHR' wherein R' is alkyl, as defined herein. The term "aminoalkyl" refers to a group having the structure $NH_2$R'—, wherein R' is alkyl, as defined herein. In certain embodiments, the alkyl group contains about 1-20 aliphatic carbon atoms. In certain other embodiments, the alkyl group contains about 1-10 aliphatic carbon atoms. In yet other embodiments, the alkyl, alkenyl, and alkynyl groups employed in the invention contain about 1-8 aliphatic carbon atoms. In still other embodiments, the alkyl group contains about 1-6 aliphatic carbon atoms. In yet other embodiments, the alkyl group contains about 1-4 aliphatic carbon atoms. Examples of alkylamino include, but are not limited to, methylamino, ethylamino, iso-propylamino and the like.

The terms "halo" and "halogen" as used herein refer to an atom selected from fluorine, chlorine, bromine and iodine.

The term "acyloxy", as used herein, does not substantially differ from the common meaning of this term in the art, and refers to a moiety of structure —OC(O)$R_X$, wherein $R_X$ is a substituted or unsubstituted aliphatic, alicyclic, heteroaliphatic, heteroalicyclic, aryl or heteroaryl moiety.

The term "acyl", as used herein, does not substantially differ from the common meaning of this term in the art, and refers to a moiety of structure —C(O)R$_X$, wherein R$_X$ is a substituted or unsubstituted, aliphatic, alicyclic, heteroaliphatic, heteroalicyclic, aryl or heteroaryl moiety.

The term "imine", as used herein, does not substantially differ from the common meaning of this term in the art, and refers to a moiety of structure —C(=NR$_X$)R$_Y$, wherein R$_X$ is hydrogen or an optionally substituted aliphatic, alicyclic, heteroaliphatic, heteroalicyclic, aryl or heteroaryl moiety; and R$_Y$ is an optionally substituted aliphatic, alicyclic, heteroaliphatic, heteroalicyclic, aryl or heteroaryl moiety.

As used herein, the terms "aliphatic", "heteroaliphatic", "alkyl", "alkenyl", "alkynyl", "heteroalkyl", "heteroalkenyl", "heteroalkynyl", and the like encompass substituted and unsubstituted, saturated and unsaturated, and linear and branched groups. Similarly, the terms "alicyclic", "heteroalicyclic", "heterocycloalkyl", "heterocycle" and the like encompass substituted and unsubstituted, and saturated and unsaturated groups. Additionally, the terms "cycloalkyl", "cycloalkenyl", "cycloalkynyl", "heterocycloalkyl", "heterocycloalkenyl", "heterocycloalkynyl", "aryl", "heteroaryl" and the like encompass both substituted and unsubstituted groups.

It will be appreciated that additional examples of generally applicable substitutents are illustrated by the specific embodiments shown in the Examples which are described herein, but are not limited to these Examples.

By the term "protecting group", has used herein, it is meant that a particular functional moiety, e.g., O, S, or N, is temporarily blocked so that a reaction can be carried out selectively at another reactive site in a multifunctional compound. In preferred embodiments, a protecting group reacts selectively in good yield to give a protected substrate that is stable to the projected reactions; the protecting group must be selectively removed in good yield by readily available, preferably non-toxic reagents that do not attack the other functional groups; the protecting group forms an easily separable derivative (more preferably without the generation of new stereogenic centers); and the protecting group has a minimum of additional functionality to avoid further sites of reaction. As detailed herein, oxygen, sulfur, nitrogen and carbon protecting groups may be utilized. For example, in certain embodiments, as detailed herein, certain exemplary oxygen protecting groups are utilized. These oxygen protecting groups include, but are not limited to methyl ethers, substituted methyl ethers (e.g., MOM (methoxymethyl ether), MTM (methylthiomethyl ether), BOM (benzyloxymethyl ether), PMBM or MPM (p-methoxybenzyloxymethyl ether), to name a few), substituted ethyl ethers, substituted benzyl ethers, silyl ethers (e.g., TMS (trimethylsilyl ether), TES (triethylsilylether), TIPS (triisopropylsilyl ether), TBDMS (t-butyldimethylsilyl ether), tribenzyl silyl ether, TBDPS (t-butyldiphenyl silyl ether), to name a few), esters (e.g., formate, acetate, benzoate (Bz), trifluoroacetate, dichloroacetate, to name a few), carbonates, cyclic acetals and ketals. In certain other exemplary embodiments, nitrogen protecting groups are utilized. These nitrogen protecting groups include, but are not limited to, carbamates (including methyl, ethyl and substituted ethyl carbamates (e.g., Troc), to name a few) amides, cyclic imide derivatives, N-Alkyl and N-Aryl amines, imine derivatives, and enamine derivatives, to name a few. Certain other exemplary protecting groups are detailed herein, however, it will be appreciated that the present invention is not intended to be limited to these protecting groups; rather, a variety of additional equivalent protecting groups can be readily identified using the above criteria and utilized in the present invention. Additionally, a variety of protecting groups are described in "Protective Groups in Organic Synthesis" Third Ed. Greene, T. W. and Wuts, P. G., Eds., John Wiley & Sons, New York: 1999, the entire contents of which are hereby incorporated by reference.

The term "natural amino acid side chain" as used herein refers to the side chain of any one of the common, naturally occurring L-amino acids found in naturally occurring proteins: glycine (Gly), alanine (Ala), valine (Val), leucine (Leu), isoleucine (Ile), lysine (Lys), arginine (Arg), histidine (His), proline (Pro), serine (Ser), threonine (Thr), phenylalanine (Phe), tyrosine (Tyr), tryptophan (Trp), aspartic acid (Asp), glutamic acid (Glu), asparagine (Asn), glutamine (Gln), cysteine (Cys) and methionine (Met).

The term "unnatural amino acid side chain" as used herein refers to the side chain of all amino acids which are not natural amino acids. This includes, for example, α-, β-, D-, L- amino acid residues, and compounds of the general formula

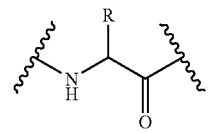

wherein the side chain R is other than the amino acid side chains occurring in nature.

More generally, the term "amino acid side chain", as used herein, encompasses natural amino acid and unnatural amino acid side chains.

As used herein, the term "pharmaceutically useful group or entity" refers to a compound or fragment thereof, or an organic moiety which, when covalently attached to a peptide or protein, can exert some biological or diagnostic function or activity when administered to a subject, or enhance the therapeutic, diagnostic or preventive properties of the parent peptide and/or protein in biomedical applications, or improve safety, alter biodegradation or excretion, or is detectable. Examples of suitable pharmaceutically useful groups or entities include hydrophilicity/hydrophobicity modifiers, pharmacokinetic modifiers, biologically active modifiers, detectable modifiers. A modifier can have one or more pharmaceutical functions, e.g., biological activity and/or pharmacokinetics modification. Pharmacokinetics modifiers can include, for example, antibodies, antigens, receptor ligands, hydrophilic, hydrophobic or charged groups. Biologically active modifiers include, for example, therapeutic drugs and prodrugs, antigens, immunomodulators. Detectable modifiers include diagnostic labels, such as radioactive, fluorescent, paramagnetic, superparamagnetic, ferromagnetic, X-ray modulating, X-ray-opaque, ultrosound-reflective, and other substances detectable by one of available clinical or laboratory methods, e.g., scintigraphy, NMR spectroscopy, MRI, X-ray tomography, sonotomography, photoimaging, radioimmunoassay. Modifiers can be small molecules or macromolecules, and can belong to any chemical or pharmaceutical class, e.g., nucleotides, chemotherapeutic agents, antibacterial agents, antiviral agents, immunomodulators, hormones or analogs thereof, enzymes, inhibitors, alkaloids and therapeutic radionuclides. Viral and non-viral gene vectors are considered to be a pharmaceutically useful entity or group.

The term "biomolecules", as used herein, refers to molecules (e.g., proteins, amino acids, peptides, polynucleotides, nucleotides, carbohydrates, sugars, lipids, nucleoproteins, glycoproteins, lipoproteins, steroids, etc.) which belong to classes of chemical compounds, whether naturally-occurring or artificially created (e.g., by synthetic or recombinant methods), that are commonly found in cells and tissues. Specific classes of biomolecules include, but are not limited to, enzymes, receptors, neurotransmitters, hormones, cytokines, cell response modifiers such as growth factors and chemotactic factors, antibodies, vaccines, haptens, toxins, interferons, ribozymes, anti-sense agents, plasmids, DNA, and RNA.

As used herein, the term "small molecule" refers to molecules, whether naturally-occurring or artificially created (e.g., via chemical synthesis) that have a relatively low molecular weight. Preferred small molecules are biologically active in that they produce a local or systemic effect in animals, preferably mammals, more preferably humans. Typically, small molecules have a molecular weight of less than about 1500 g/mol. In certain preferred embodiments, the small molecule is a drug. Preferably, though not necessarily, the drug is one that has already been deemed safe and effective for use by the appropriate governmental agency or body. For example, drugs for human use listed by the FDA under 21 C.F.R. §§ 330.5, 331 through 361, and 440 through 460; drugs for veterinary use listed by the FDA under 21 C.F.R. §§ 500 through 589, incorporated herein by reference, are all considered suitable for use with the present hydrophilic polymers.

Classes of small molecule drugs that can be used in the practice of the present invention include, but are not limited to, vitamins, anti-AIDS substances, anti-cancer substances, antibiotics, immunosuppressants, anti-viral substances, enzyme inhibitors, neurotoxins, opioids, hypnotics, anti-histamines, lubricants, tranquilizers, anti-convulsants, muscle relaxants and anti-Parkinson substances, anti-spasmodics and muscle contractants including channel blockers, miotics and anti-cholinergics, anti-glaucoma compounds, anti-parasite and/or anti-protozoal compounds, modulators of cell-extracellular matrix interactions including cell growth inhibitors and anti-adhesion molecules, vasodilating agents, inhibitors of DNA, RNA or protein synthesis, anti-hypertensives, analgesics, anti-pyretics, steroidal and non-steroidal anti-inflammatory agents, anti-angiogenic factors, anti-secretory factors, anticoagulants and/or antithrombotic agents, local anesthetics, ophthalmics, prostaglandins, anti-depressants, anti-psychotic substances, anti-emetics, imaging agents. Many large molecules are also drugs.

A more complete, although not exhaustive, listing of classes and specific drugs suitable for practicing the present invention may be found in "Pharmaceutical Substances: Syntheses, Patents, Applications" by Axel Kleemann and Jurgen Engel, Thieme Medical Publishing, 1999 and the "Merck Index: An Encyclopedia of Chemicals, Drugs, and Biologicals", Edited by Susan Budavari et al., CRC Press, 1996, both of which are incorporated herein by reference.

As used herein, the term "macromolecules" refers to molecules, whether naturally-occurring or artificially created (e.g., via chemical synthesis) that have a relatively high molecular weight, e.g., generally above 1500 g/mole. Preferred macromolecules are biologically active in that they exert a biological function in animals, preferably mammals, more preferably humans. Examples of macromolecules include proteins, enzymes, growth factors, cytokines, peptides, polypeptides, polylysine, proteins, lipids, polyelectrolytes, immunoglobulins, DNA, RNA, ribozymes, plasmids, and lectins. For the purpose of this invention, supramolecular constructs such as viruses and protein associates (e.g., dimers) are considered to be macromolecules. When covalently attached to a peptide or protein, a macromolecule may be chemically modified prior to being covalently attached to said peptide or protein.

As used herein, the term "diagnostic label" refers to an atom, group of atoms, moiety or functional group, a nanocrystal, or other discrete element of a composition of matter, that can be detected in vivo or ex vivo using analytical methods known in the art. When covalently attached to a peptide or protein, such diagnostic labels permit the monitoring of the peptide or protein in vivo. On the other hand, constructs and compositions that include diagnostic labels can be used to monitor biological functions or structures. Examples of diagnostic labels include, without limitations, labels that can be used in medical diagnostic procedures, such as, radiopharmaceutical or radioactive isotopes for gamma scintigraphy and Positron Emission Tomography (PET), contrast agent for Magnetic Resonance Imaging (MRI) (for example paramagnetic atoms and superparamagnetic nanocrystals), contrast agent for computed tomography, contrast agent for X-ray imaging method, agent for ultrasound diagnostic method, agent for neutron activation, and moiety which can reflect, scatter or affect X-rays, ultrasounds, radiowaves and microwaves, fluorophores in various optical procedures, etc.

DETAILED DESCRIPTION OF CERTAIN PREFERRED EMBODIMENTS OF THE INVENTION

Figure 1:
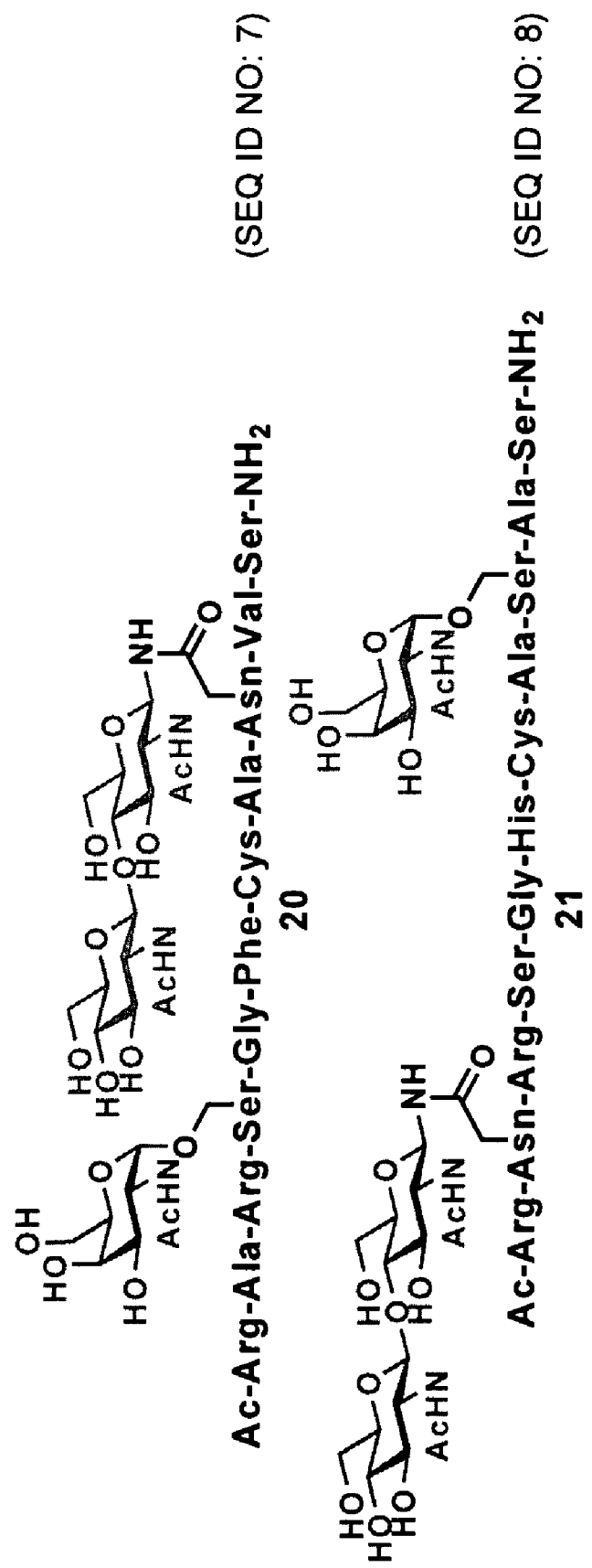
FIG. 1 depicts examples of bifunctional glycopeptides (i.e., diglycosylated peptides) containing O-linkages preparaed by the method of the invention.

In one aspect, the present invention provides novel methodologies for the synthesis of peptides and/or proteins functionalized at two or more non-adjacent amino acid sites (e.g., bearing a pharmaceutically useful group or entity covalently attached to at least two non-adjacent amino acid residues of the polypeptide/protein chain). In certain embodiments, the invention provides a system for the synthesis of polypeptides and proteins bearing at least two glycans covalently attached to non-adjacent amino acid residues of the polypeptide/protein chain. In certain embodiments, in the context of synthetic studies developed for the total synthesis of glycosylated fragments of erythropoietin, generalized methodologies were developed for the improved synthesis of polyglycosylated peptides and proteins. This general synthetic method encompasses the realization that native chemical ligation (NCL) is a glycan-compatible process that may be used for assembling large multiply glycosylated polypeptides from glycopeptide building blocks. In yet another aspect, the present invention also provides the recognition that chemoselective reaction of a glycopeptide containing a C-terminal cysteine with a glycopeptide thioester may be achieved to from the corresponding diglycosylated peptide adduct.

Specific examples, particularly with respect to the synthesis of bifunctional glycopeptides (i.e., diglycosylated peptides), are described in more detail below and in the Exemplification herein, along with certain general methodologies developed during the course of these syntheses. It will be appreciated by one of ordinary skill in the art that these examples are not intended to be limiting; rather all equivalents are intended to be incorporated into the scope of the present invention. In particular, the inventive method may be generally adapted to the preparation of polyfunctionalized peptides and proteins.

1) Description of Certain Embodiments of the Inventive Method

In one aspect of the present invention, there is provided a method for preparing a polyfunctionalized peptide comprising a peptidic backbone made up of four or more amino acids wherein two or more non-adjacent amino acids are independently substituted with a moiety having the structure:

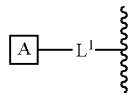

wherein each occurrence of $L^1$ is independently a substituted or unsubstituted, linear or branched, cyclic or acyclic, saturated or unsaturated aliphatic or heteroaliphatic moiety;
each occurrence of A is independently an aliphatic, heteroaliphatic, aromatic, heteroaromatic, aryl, heteroaryl or a pharmaceutically useful group or entity;
with the proviso that the peptide sequence between any two consecutive, non-adjacent, amino acids bearing a A-$L^1$- moiety comprises at least one cysteine residue.

In one aspect of the present invention, there is provided a method for preparing a polyfunctionalized peptide comprising a peptidic backbone made up of four or more amino acids wherein two or more non-adjacent amino acids are independently substituted with a moiety having the structure:

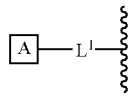

with the proviso that the peptide sequence between any two consecutive, non-adjacent, amino acids bearing a A-$L^1$- moiety comprises at least one cysteine residue;
wherein the method comprises a step of:
reacting a peptide acyl donor comprising a peptidic backbone made up of two or more amino acids wherein said peptide acyl donor has the structure:

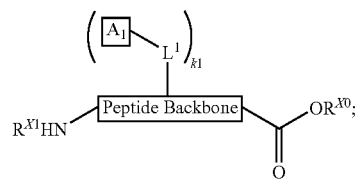

with a peptide amine acceptor having the structure:

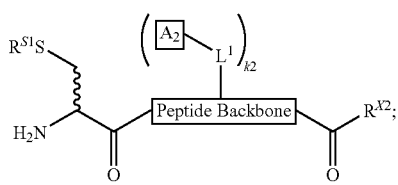

under suitable conditions to effect ligation;
wherein k1 and k2 are independently integers between 1 and about 20;
each occurrence of A, $A_1$ and $A_2$ is independently an aliphatic, heteroaliphatic, aromatic, heteroaromatic, aryl, heteroaryl or a pharmaceutically useful group or entity;
$R^{S1}$ is a sulfide protecting group;
$R^{X0}$ is a group such that the moiety —C(=O)$OR^{X0}$ can be made to undergo ligation with the peptide amine acceptor;
each occurrence of $L^1$ is independently a substituted or unsubstituted, linear or branched, cyclic or acyclic, saturated or unsaturated aliphatic or heteroaliphatic moiety;
$R^{X1}$ is hydrogen, alkyl, acyl, aromatic, heteroaromatic, aryl, heteroaryl, -alkyl(aryl), -alkyl(heteroaryl), a nitrogen protecting group, an amino acid or a proctected amino acid; and
$R^{X2}$ is —$OR^{X2a}$ or —$NR^{X2b}R^{X2c}$, wherein $R^{X2a}$ is hydrogen, alkyl, aromatic, heteroaromatic, aryl, heteroaryl, -alkyl(aryl), -alkyl(heteroaryl), a carboxylic acid protecting group, an amino acid or a proctected amino acid; and $R^{X2b}$ and $R^{X2c}$ are independently hydrogen, alkyl, aromatic, heteroaromatic, aryl, heteroaryl, -alkyl(aryl), -alkyl(heteroaryl), a nitrogen protecting group, an amino acid or a proctected amino acid.

In certain embodiments, each occurrence of A is independently a pharmaceutically useful group or entity. In certain embodiments, each occurrence of A is independently a biomolecule, a small molecule, a macromolecule or a diagnostic label.

In certain exemplary embodiments, each occurrence of A is independently a carbohydrate determinant having the structure:

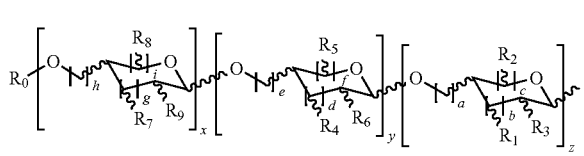

wherein a, b, c, d, e, f, g, h, i, x, y and z are independently 0, 1, 2 or 3, with the proviso that the x, y and z bracketed structures represent furanose or pyranose moieties and the sum of b and c is 1 or 2, the sum of d and f is 1 or 2, and the sum of g and i is 1 or 2, and with the proviso that x, y and z are not simultaneously 0; wherein $R_0$ is hydrogen, a linear or branched chain alkyl, acyl, arylalkyl or aryl group; wherein each occurrence of $R_1$, $R_2$, $R_3$, $R_4$, $R_5$, $R_6$, $R_7$, $R_8$ and $R_9$ is independently hydrogen, OH, $OR^i$, $NHR^i$, $NHCOR^i$, F, $CH_2OH$, $CH_2OR^i$, a substituted or unsubstituted linear or branched chain alkyl, (mono-, di- or tri)hydroxyalkyl, (mono-, di- or tri)acyloxyalkyl, arylalkyl or aryl group; wherein each occurrence of $R^i$ is independently hydrogen, CHO, $COOR^{ii}$, or a substituted or unsubstituted linear or branched chain alkyl, acyl, arylalkyl or aryl group or a saccharide moiety having the structure:

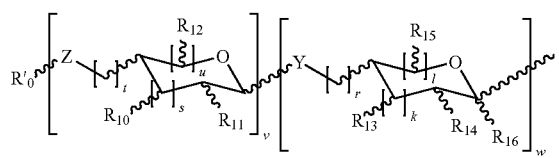

wherein Y and Z are independently NH or O; wherein k, l, r, s, t, u, v and w are each independently 0, 1 or 2; with the proviso that the v and w bracketed structures represent furanose or pyranose moieties and the sum of 1 and k is 1 or 2, and the sum of s and u is 1 or 2, and with the proviso that v and w are not simultaneously 0; wherein $R'_0$ is hydrogen, a linear or branched chain alkyl, acyl, arylalkyl or aryl group; wherein each occurrence of $R_{10}$, $R_{11}$, $R_{12}$, $R_{13}$, $R_{14}$ and $R_{15}$ is independently hydrogen, OH, $OR^{iii}$, $NHR^{iii}$, $NHCOR^{iii}$, F, $CH_2OH$, $CH_2OR^{iii}$, or a substituted or unsubstituted linear or branched chain alkyl, (mono-, di- or tri)hydroxyalkyl, (mono-, di- or tri)acyloxyalkyl, arylalkyl or aryl group; wherein each occurrence of $R_{16}$ is hydrogen, COOH, $COOR^{ii}$, $CONHR^{ii}$, a substituted or unsubstituted linear or branched chain alkyl or aryl group; wherein each occurrence of $R^{iii}$ is hydrogen, CHO, $COOR^{iv}$, or a substituted or unsubstituted linear or branched chain alkyl, acyl, arylalkyl or aryl group; and wherein each occurrence of $R^{ii}$ and $R^{iv}$ are each independently H, or a substituted or unsubstituted linear or branched chain alkyl, arylalkyl or aryl group.

In certain embodiments, $L^1$ may comprise any functional moiety that is compatible with native chemical ligation reaction conditions. In certain embodiments, $L^1$ may comprise any functional moiety that is compatible with aqueous conditions. In certain embodiments, a compatible functionality is one that is stable, unreactive and/or minimally interferes with the reaction. A thiol group is considered a compatible functionality, even though a thiol group may slow down the reaction. Examples of suitable functionalities include, but are not limited to, hydrocarbons, amines, amides, imines, hydroxyls, ethers, carboxylic esters, aldehydes, thiols, olefins, alkynes, aryls and heteroaryls. In certain exemplary embodiments, $L^1$ does not comprise a thiol group.

In certain embodiments, each occurrence of $L^1$ is independently —O—$(CH_2)_n$—, wherein n is 0-9, or a glycoside-containing moiety (e.g mono- or poly-saccharide).

In certain embodiments, each occurrence of $L^1$ is —O—$(CH_2)_n$—$CH_2$— and two or more non-adjacent amino acids is/are independently substituted with a moiety having the structure:

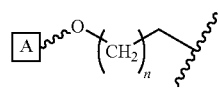

wherein each occurrence of n is independently 0-8; and A is as defined above. In certain other embodiments, A is a carbohydrate moiety and each occurrence of the n-alkyl glycosidic moiety is independently either α- or β-linked to an amino acid residue of the backbone. It will be appreciated that polyfunctionalized peptides made according to the method of the present invention are not limited to those where each occurrence of $L^1$ comprises n-alkyl where n is greater than or equal to 1; rather each occurrence of A can be independently linked via the traditional direct linkage (n=0), via n-alkyl (such as pentyl), via a mono-saccharide moiety or any combination thereof. In preferred embodiments, each occurrence of A is independently selected from the group consisting of Globo-H, fucosyl GM1, KH-1, glycophorin, STN, (2,3) ST, $Le^y$, $Le^x$, N3, Tn, 2,6-STn, Gb3 and TF.

In certain embodiments, occurrences of A may be the same or different.

In certain other embodiments, certain occurrences of A are clustered. For example, in certain embodiments, the polyfunctionalized peptide comprises at least two adjacent functionalized amino acids (i.e., clustered functionalized amino acids), separated from another functionalized site by a peptide amino acid sequence comprising at least one cysteine residue.

In certain other embodiments, certain occurrences of A are clustered glycosides. For example, in certain embodiments, the multiglycosylated peptide comprises at least two adjacent glycosylated amino acids (i.e., clustered glycosylated amino acids), separated from another glycosylated site by a peptide amino acid sequence comprising at least one cysteine residue.

In certain embodiments, the present invention provides a method for preparing a polyfunctionalized peptide having the structure:

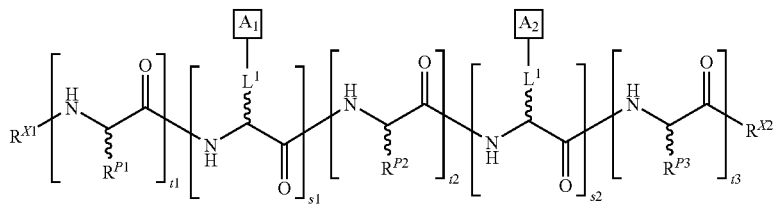

s1 and s2 independently an integer from 1 to about 20;
t1, t2 and t3 are each independently an integer;
$R^{X1}$ is hydrogen, alkyl, acyl, aromatic, heteroaromatic, aryl, heteroaryl, -alkyl(aryl), -alkyl(heteroaryl), a nitrogen protecting group, an amino acid or a proctected amino acid;
$R^{X2}$ is —$OR^{X2a}$ or —$NR^{X2b}R^{X2c}$, wherein $R^{X2a}$ is hydrogen, alkyl, aromatic, heteroaromatic, aryl, heteroaryl, -alkyl(aryl), -alkyl(heteroaryl), a carboxylic acid protecting group, an amino acid or a proctected amino acid; and $R^{X2b}$ and $R^{X2c}$ are independently hydrogen, alkyl, aromatic, heteroaromatic, aryl, heteroaryl, -alkyl(aryl), -alkyl(heteroaryl), a nitrogen protecting group, an amino acid or a proctected amino acid;
$R^{P1}$, $R^{P2}$ and $R^{P3}$ are independently H, alkyl, heteroalkyl, aromatic, heteroaromatic, aryl, heteroaryl, -alkyl(aryl), -alkyl(heteroaryl), or a natural or non-natural amino acid side chain;
each occurrence of $L^1$ is independently a substituted or unsubstituted aliphatic or heteroaliphatic moiety;
$A_1$ and $A_2$ are each independently an aliphatic, heteroaliphatic, aromatic, heteroaromatic, aryl, heteroaryl or a pharmaceutically useful group or entity; and
at least one occurrence of the bracketed structure t2 is a cysteine residue or protected cysteine residue;

wherein the method comprises a step of:
reacting a peptide acyl donor having the structure:

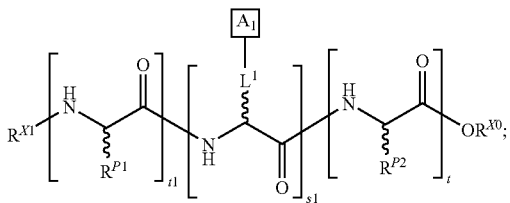

with a peptide amine acceptor having the structure:

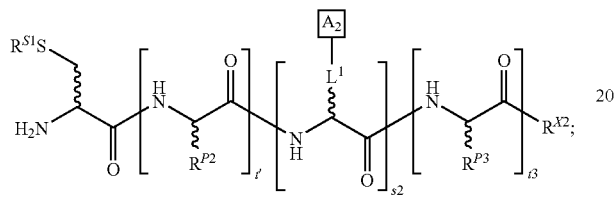

under suitable conditions to effect ligation;
wherein the sum $t+t'$ equals $(t2)+1$; $R^{S1}$ is a sulfide protecting group; and $R^{X0}$ is a group such that the moiety —(=O)OR$^{X0}$ can be made to undergo ligation with the glycopeptide amine acceptor.

In certain exemplary embodiments, $A_1$ and $A_2$ are each independently a carbohydrate domain having the structure:

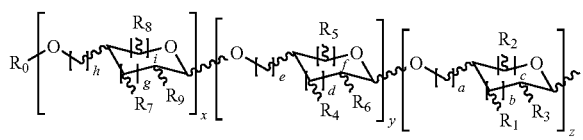

wherein a, b, c, d, e, f, g, h, i, x, y and z are independently 0, 1, 2 or 3, with the proviso that the x, y and z bracketed structures represent furanose or pyranose moieties and the sum of b and c is 1 or 2, the sum of d and f is 1 or 2, and the sum of g and i is 1 or 2, and with the proviso that x, y and z are not simultaneously 0; wherein $R_0$ is hydrogen, a linear or branched chain alkyl, acyl, arylalkyl or aryl group; wherein each occurrence of $R_1$, $R_2$, $R_3$, $R_4$, $R_5$, $R_6$, $R_7$, $R_8$ and $R_9$ is independently hydrogen, OH, OR$^i$, NHR$^i$, NHCOR$^i$, F, CH$_2$OH, CH$_2$OR$^i$, a substituted or unsubstituted linear or branched chain alkyl, (mono-, di- or tri)hydroxyalkyl, (mono-, di- or tri)acyloxyalkyl, arylalkyl or aryl group; wherein each occurrence of R$^i$ is independently hydrogen, CHO, COOR$^{ii}$, or a substituted or unsubstituted linear or branched chain alkyl, acyl, arylalkyl or aryl group or a saccharide moiety having the structure:

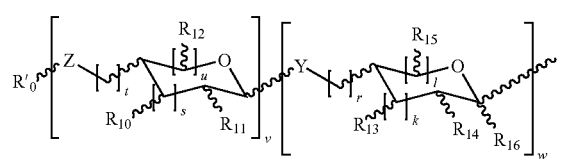

wherein Y and Z are independently NH or O; wherein k, l, r, s, t, u, v and w are each independently 0, 1 or 2; with the proviso that the v and w bracketed structures represent furanose or pyranose moieties and the sum of l and k is 1 or 2, and the sum of s and u is 1 or 2, and with the proviso that v and w are not simultaneously 0; wherein $R'_0$ is hydrogen, a linear or branched chain alkyl, acyl, arylalkyl or aryl group; wherein each occurrence of $R_{10}$, $R_{11}$, $R_{12}$, $R_{13}$, $R_{14}$ and $R_{15}$ is independently hydrogen, OH, OR$^{iii}$, NHR$^{iii}$, NHCOR$^{iii}$, F, CH$_2$OH, CH$_2$OR$^{iii}$, or a substituted or unsubstituted linear or branched chain alkyl, (mono-, di- or tri)hydroxyalkyl, (mono-, di- or tri)acyloxyalkyl, arylalkyl or aryl group; wherein each occurrence of $R_{16}$ is hydrogen, COOH, COOR$^{ii}$, CONHR$^{ii}$, a substituted or unsubstituted linear or branched chain alkyl or aryl group; wherein each occurrence of R$^{iii}$ is hydrogen, CHO, COOR$^{iv}$, or a substituted or unsubstituted linear or branched chain alkyl, acyl, arylalkyl or aryl group; and wherein each occurrence of R$^{ii}$ and R$^{iv}$ are each independently H, or a substituted or unsubstituted linear or branched chain alkyl, arylalkyl or aryl group; and wherein each glycosidic moiety is either α- or β-linked to an amino acid.

In certain embodiments, the step may be carried out once, or repeated a desired number of times, to prepare a polyfunctionalized peptide having the structure:

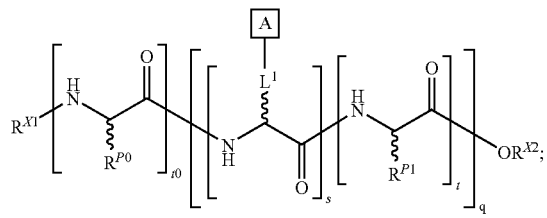

wherein $R^{X1}$ and $R^{X2}$ are as defined above;
each occurrence of A may be the same or different and may be as defined for $A_1$ and $A_2$ above;
each occurrence of $R^{P1}$ may be the same or different and may be as defined for $R^{P1}$ and $R^{P2}$ above;
q is an integer greater than or equal to 2;
each occurrence of s is independently an integer from 1 to about 20;
each occurrence of t is independently an integer;
t0 is an integer; and
each occurrence of $R^{P0}$ is independently H, alkyl, heteroalkyl, aromatic, heteroaromatic, aryl, heteroaryl, -alkyl(aryl), -alkyl(heteroaryl), or a natural or non-natural amino acid side chain.

In certain embodiments, q is an integer between 2 and about 5. In certain embodiments, q is an integer between 2 and about 10. In certain embodiments, q is an integer between 2 and about 15. In certain embodiments, q is an integer between 2 and about 20. In certain embodiments, q is an integer between 2 and about 25. In certain embodiments, q is an integer between 2 and about 30. In certain embodiments, q is an integer greater than 30. In certain embodiments, q is 2.

In certain embodiments, the sum s+t is between about 2 and about 6.

In certain embodiments, the sum s+t is between about 2 and about 10. In certain embodiments, the sum s+t is between about 2 and about 15. In certain embodiments, the sum s+t is between about 2 and about 20. In certain embodiments, the sum s+t is between about 2 and about 50. In certain embodiments, the sum s+t is between about 2 and about 100. In certain embodiments, the sum s+t is between about 2 and about 150. In certain embodiments, the sum s+t is between about 2 and about 200. In certain embodiments, the sum s+t may be greater than 200.

In certain embodiments, t0 is an integer from 0 to about 2. In certain embodiments, t0 is an integer from 0 to about 5. In certain embodiments, t0 is an integer from 0 to about 10. In certain embodiments, t0 is an integer from 0 to about 15. In certain embodiments, t0 is an integer from 0 to about 20. In certain embodiments, t0 is an integer from 0 to about 25. In certain embodiments, t0 is an integer from 0 to about 30. In certain embodiments, t0 is an integer from 0 to about 50. In certain embodiments, t0 is an integer from 0 to about 100. In certain embodiments, t0 is an integer from 0 to about 150. In certain embodiments, t0 is an integer from 0 to about 200. In certain embodiments, t0 is an integer greater than 200.

In certain other embodiments, $R^{X1}$ is hydrogen, Fmoc or Ac.

In certain other embodiments, $R^{X2}$ is $NH_2$.

In certain other embodiments, $R^{X0}$ is a sulfur-substituted aryl moiety.

In certain embodiments, $R^{X0}$ is a disulfide-substituted aryl moiety. In certain embodiments, $R^{X0}$ has the structure:

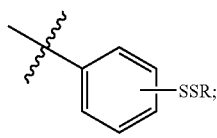

wherein R is an aliphatic, heteroaliphatic, aromatic or heteroaromatic moiety.

In certain exemplary embodiments, $R^{X0}$ has the structure:

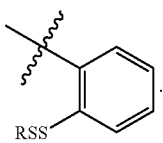

In certain embodiments, R is lower alkyl. In certain exemplary embodiments, R is ethyl.

In certain other embodiments, $R^{S1}$ is -StBu.

In certain exemplary embodiments, in the step of reacting the peptide acyl donor having the structure:

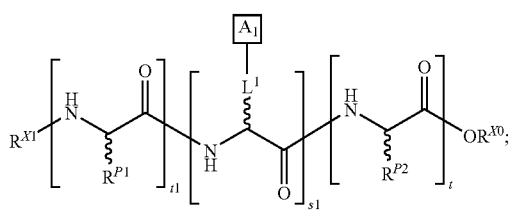

with the peptide amine acceptor under suitable conditions to effect ligation, an intermediate having the following structure is formed in situ:

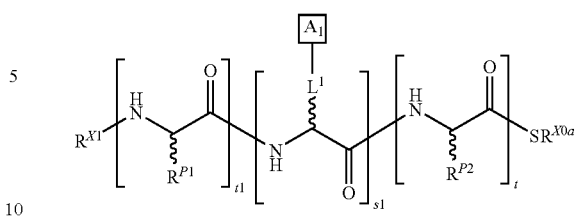

wherein $R^{X0a}$ is an oxygen-substituted aryl moiety.

In certain embodiments, the suitable conditions to effect ligation comprise MES-Na.

In certain exemplary embodiments, in the peptide acyl donor having the structure:

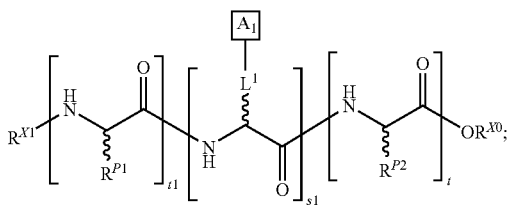

the amino acyl residue directly attached to $-OR^{X0}$ is phenylalanine.

In certain embodiments, A may comprise any functional moiety that is compatible with native chemical ligation reaction conditions. In certain embodiments, A may comprise any functional moiety that is compatible with aqueous conditions. In certain embodiments, a compatible functionality is one that is stable, unreactive and/or minimally interferes with the reaction. A thiol group is considered a compatible functionality, even though a thiol group may slow down the reaction. Examples of suitable functionalities include, but are not limited to, hydrocarbons, amines, amides, imines, hydroxyls, ethers, carboxylic esters, aldehydes, thiols, olefins, alkynes, aryls and heteroaryls. In certain exemplary embodiments, A does not comprise a thiol group.

In certain embodiments, when at least one occurrence of A (or $A_1$ and/or $A_2$, as further defined for A) is a carbohydrate domain, some or all of carbohydrate domains are O-linked to the peptide backbone. In certain other embodiments, when at least one occurrence of A (or $A_1$ and/or $A_2$, as further defined for A) is a carbohydrate domain, some or all of carbohydrate domains are N-linked to the peptide backbone. In certain other embodiments, when at least one occurrence of A (or $A_1$ and/or $A_2$, as further defined for A) is a carbohydrate domain, the inventive method may be praticed while the carbohydrate domain is partially or fully deprotected (i.e., comprises exposed OH groups). In certain embodiments, the peptide sequence between each point of attachment of the A moieties comprises a cysteine residue. In certain embodiments, the polyfunctionalized construct (i.e., construct bearing more than one A moiety) is prepared by Native Chemical Ligation. In certain embodiments, the polyfunctionalized peptides obtained by the inventive method are symmetrical (functionalized peptide building blocks to be ligated have the same peptide sequence (safe for N- and/or C-terminals) and bear the same functionalization pattern), nonsymmetrical (functionalized peptide building blocks to be ligated differ in peptide sequence (excluding N- and C-terminals) and/or functionalization pattern). In certain embodiments, the inventive method allows the preparation of multiglycosylated peptides designed to approximate the spatial position(s) of carbohydrate(s) in glycoprotein/glycopeptides of interest (e.g., naturally occurring glycoproteins such as gp120 and erythropoietin).

In certain embodiments, the method further comprises a step of conjugating the polyfunctionalized peptide to an immunogenic carrier. In certain exemplary embodiments, the carrier is a protein, a peptide or a lipid. In certain other exemplary embodiments, the carrier is Bovine Serum Albumin (BSA), Keyhole Limpet Hemocyanin (KLH) or polylysine. In certain other embodiments, the carrier is a lipid carrier having the structure:

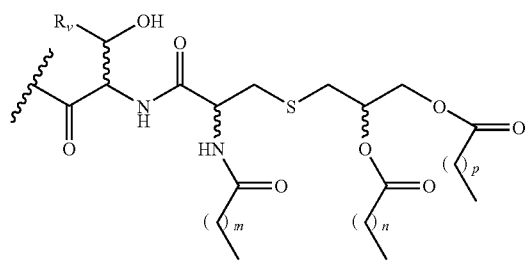

wherein m, n and p are each independently integers between about 8 and 20; and $R_v$ is hydrogen, substituted or unsubstituted linear or branched chain lower alkyl or substituted or unsubstituted phenyl. In certain exemplary embodiments, m', n' and p' are each 14 and the lipid is tripalmitoyl-S-glycerylcysteinylserine (e.g., Pam-Cys).

It will be appreciated that the carrier can be linked to the polyfunctionalized peptide either directly or through a crosslinker, and thus the peptide may be attached to a protein, peptides, or lipid, as well as a (crosslinker-protein), (crosslinker-peptide) and (crosslinker-lipid) moiety.

Crosslinkers suited to the invention are widely known in the art (see, for example, 1994 Pierce Technical Handbook: cross-linking (Appendix A), which is available at http://www.piercenet.com/resources/browse.cfm?fldID-184), including bromoacetic NHS ester, 6-(iodoacetamido)caproic acid NHS ester, maleimidoacetic acid NHS ester, maleimidobenzoic acide NHS ester, etc. In certain preferred embodiments, the crosslinker is MMCCH (4-(maleimidomethyl) cyclohexane-1-carboxyl hydrazide). In certain other preferred embodiments, the crosslinker is MBS (m-maleimidobenzoyl acid N-Hydroxysuccinimidyl ester). In certain embodiments, the crosslinker is a fragment having the structure:

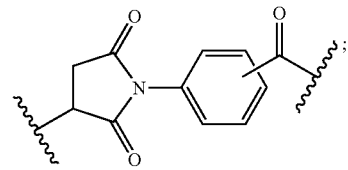

whereby said structure is generated upon conjugation of a maleimidobenzoic acid N-hydroxy succinimide ester with a suitable functionality on the polyfunctionalized peptide.

2) Exemplary Synthetic Methodology

Native Chemical Ligation

One of the more widely used methods for the synthesis of glycopeptides is native chemical ligation (NCL).[48] First reported by Kent in 1994, NCL allows for the assembly of large proteins with native amide bonds from unprotected peptide building blocks (Scheme 1). Furthermore, the reaction is mild, selective, and compatible with the presence of glycans. When glycans are present in the reaction, they are typically found on the C-terminal side. In the event, a glycopeptide containing a C-terminal cysteine undergoes a chemoselective reaction with a peptide thioester. The resulting peptide thioester then rearranges spontaneously to furnish a native peptide bond, effectively lengthening the peptide backbone of the glycopeptide.

Scheme 1.
Exemplary Native Chemical Ligation methodology

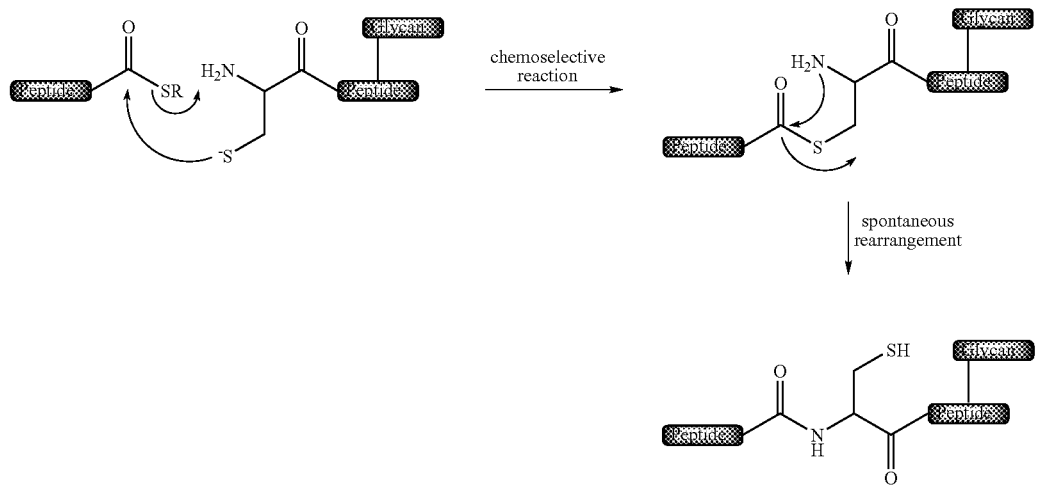

As discussed above, glycopeptides bearing multiple glycosidic domains are of particular interest. Such structures include the synthesis of gp120 fragments, erythropoietin (EPO), human chorionic gonadotropin (HCG), and amyloid precursor protein (APP). Drawing from previous studies in the area,[49] NCL was explored as a way to couple two small glycopeptides to form one large glycopeptide. One drawback that became apparent lies in the difficulty with which unprotected glycopeptide α-thioesters are synthesized.[50] Accordingly, a new method for the synthesis of glycopeptide α-thioesters, or their equivalent, was devised, to allow the assembly of glycopeptides bearing multiple glycosidic domains.

A closer look at the reaction mechanism of NCL provided clues as to how this problem might be approached. In one embodiment of the reaction itself, the sulfhydryl group of the cysteine coupling partner, initially protected as a t-butyldisulfide, is released by disulfide exchange with 2-mercaptoethanesulfonic acid (MESNa) and then undergoes trans-thioesterification as mentioned above. Without wishing to be bound to any particular theory, it was thought that it might be possible to mask the α-thioester as a phenyl ester, bearing an ethyldisulfide in the ortho position (Scheme 2) by taking advantage of this disulfide exchange. Under the reaction conditions, the free sulfhydryl would be released and undergo a spontaneous rearrangement to furnish a thioester capable of entering into the NCL pathway.

To test the viability of this proposed modification, the simple dipeptide, PheCys, was synthesized. The desired ortho-substituted phenol was synthesized in two steps from commercially available 2-mercaptophenol by oxidation and disulfide exchange. Coupling of the phenol to phenylalanine followed by the removal of the Boc protecting group set the stage for our first attempt (Scheme 3). The reaction proceeded in good yield. More importantly no racemization was observed under the reaction conditions.

Scheme 3.
Exemplary NCL with masked thioester

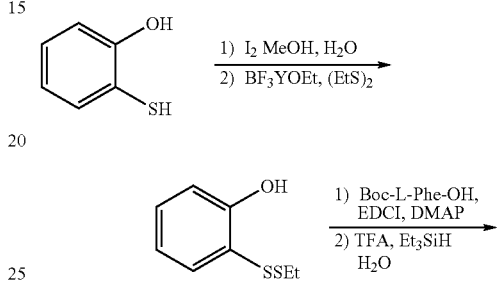

Scheme 2.
A new method for the generation of peptide α-thioesters.

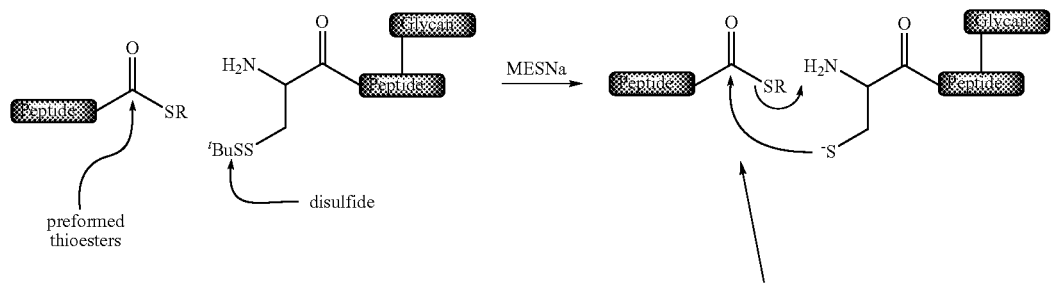

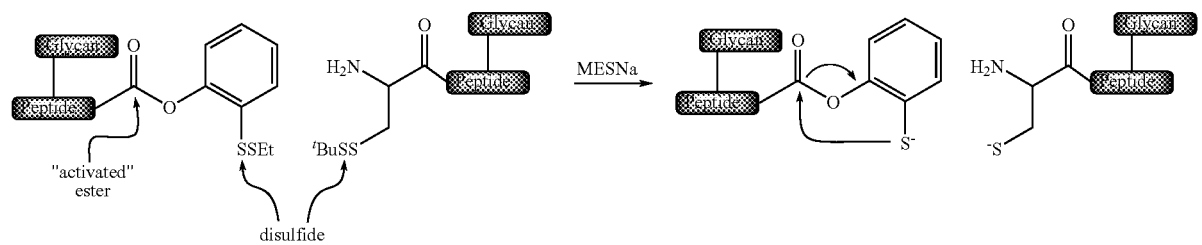

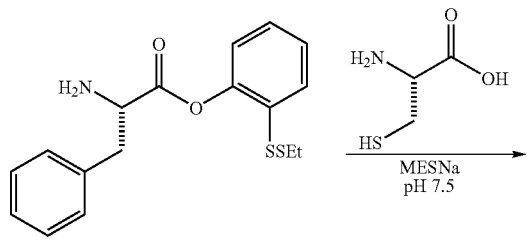

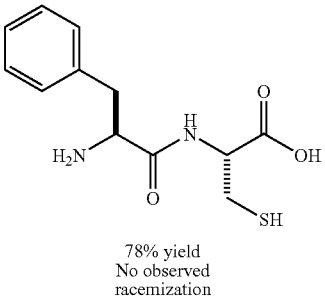

78% yield
No observed racemization

The synthesis of glycopeptides bearing two glycosidic domains was then undertaken. Synthesis of the N-terminal fragment (the fragment that would ultimately become the masked thioester) began with the solid phase synthesis of a peptide acid, followed by standard peptide coupling to introduce the phenylalanine bearing the phenyl ester. TFA deprotection of the side chain protecting groups furnished the peptide backbone for the N-terminal fragment (Scheme 4).

Scheme 4.
Exemplary synthesis of the peptide backbone of the N-terminal fragment.

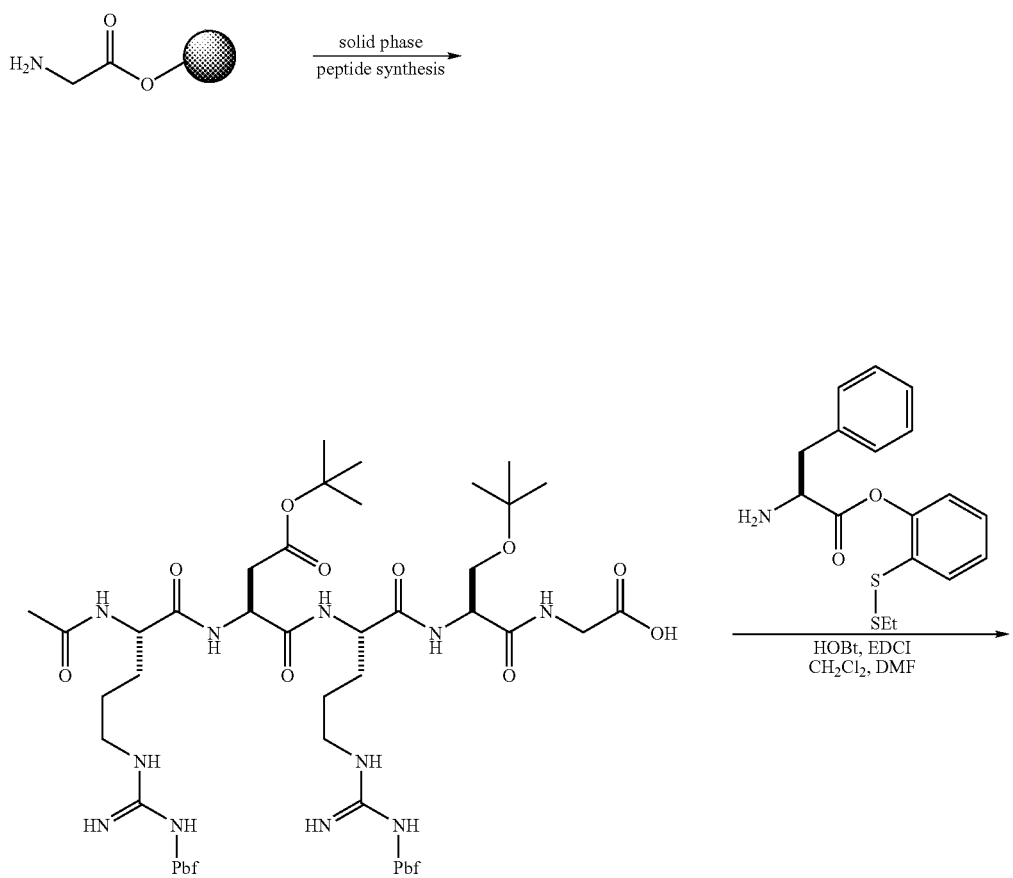

(SEQ ID NO: 1)

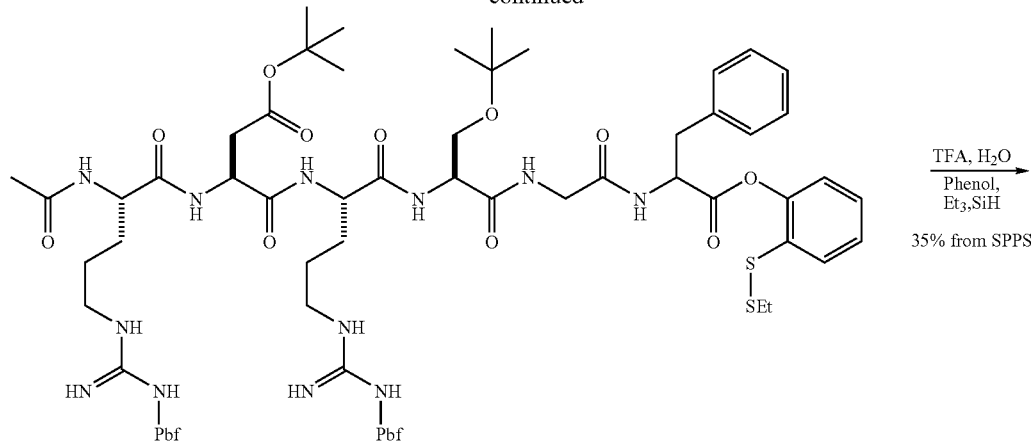
(SEQ ID NO: 2)
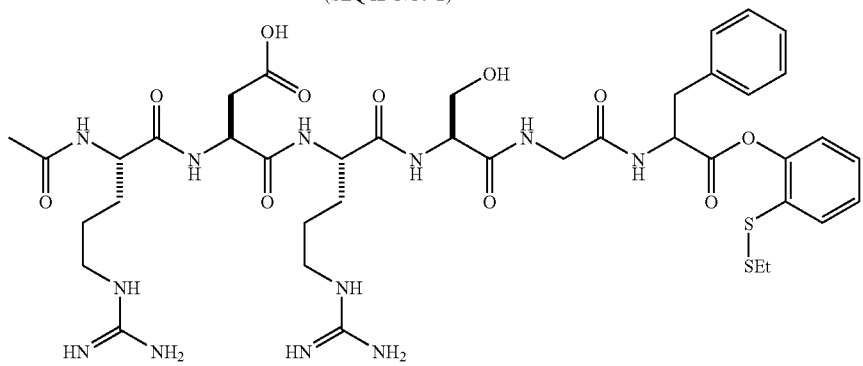
(SEQ ID NO: 2)
Coupling of an oligosaccharide with excess peptide furnished a fully deprotected glycopeptide ready for ligation (Scheme 5).
Scheme 5.
Exemplary approach to the completion of the N-terminal fragment
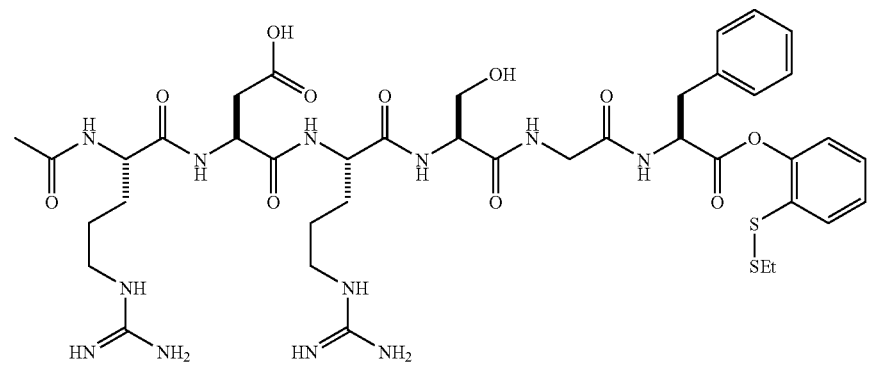
(SEQ ID NO: 2)
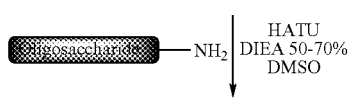

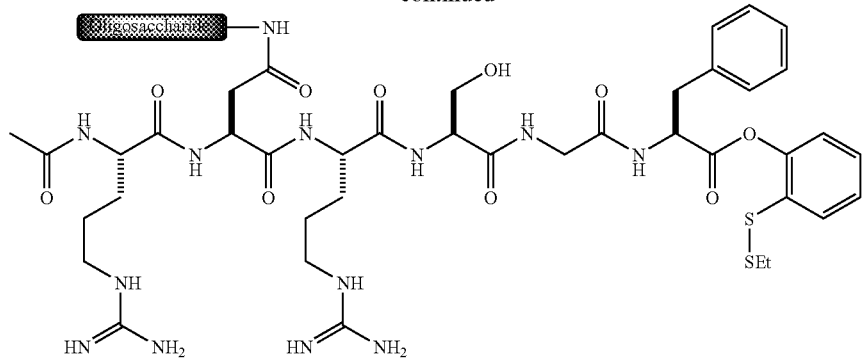

(SEQ ID NO: 3)

With the N-terminal portion in hand, the synthesis of the C-terminal coupling partner was then carried out. In a similar way, the peptide backbone was prepared by solid phase peptide synthesis. Upon cleavage from the resin, glycosylation and Fmoc removal, the C-terminal glycopeptide was obtained (Scheme 6).

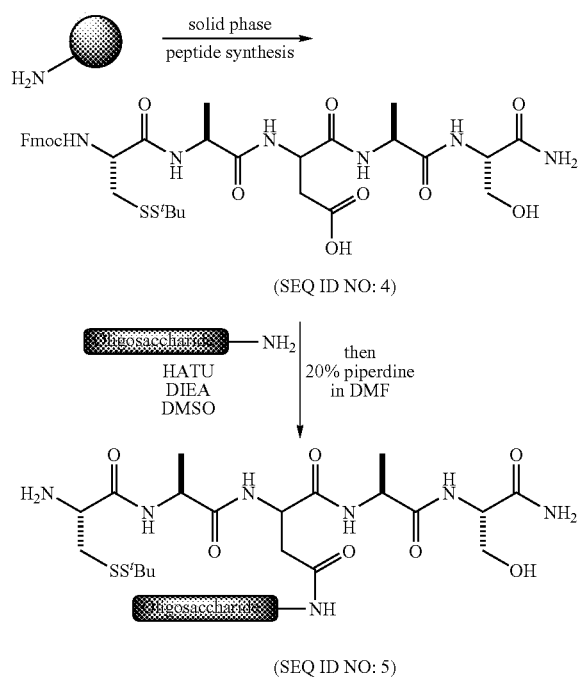

In certain exemplary embodiments, the synthesis of glycopeptides bearing two glycosydic domains was accomplished as follows: equal molar amounts of both the N-terminal and C-terminal glycopeptides were combined in a LCMS vial and to this was added a solution of MESNa in phosphate buffered saline. The reaction was monitored by LCMS and to our amazement, the rearrangement of the phenyl ester to thioester occurred quite rapidly,[51] additionally mass peaks corresponding to the desired product were observed almost instantly.

Upon completion of the reaction, any remaining disulfide bonds were reduced by the action of tris(2-carboxyethyl) phosphine hydrochloride (TCEP). The crude reaction mixture was then subjected to HPLC for purification. The reaction proceeded extremely well, providing doubly glycosylated glycopeptides, typically in 60-70% yield. Exemplary di-glycosylated peptides that may be prepared by the method of the present invention are detailed in the Exemplification below. It should be noted that symmetrical, non-symmetrical and mixed (N-linked and O-linked) glycopeptides can be used.

Accordingly, there is provided herein a method for preparing glycopeptides comprising at least two carbohydate domains covalently attached thereto. In certain embodiments, some or all of carbohydrate domains are O-linked. In certain other embodiments, some or all of carbohydrate domains are N-linked. In certain embodiments, the glycopeptide comprises two or more carbohydate domains covalently attached thereto, wherein the glycopeptide sequence between each point of attachment of the carbohydrate domains comprises a cysteine residue. In certain embodiments, the mutli-glycan glycopeptide is prepared by Native Chemical Ligation. In certain embodiments, the method allows for coupling where each coupling partner is a glycopeptide itself. Symmetrical, nonsymmetrical and mixed (N-linked and O-linked) glycopeptides can be obtained. In certain embodiments, the method involves the in situ generation of a thioester that is then used immediately in native chemical ligation.

Peptide Thioester Synthesis

Several methods have been developed for peptide thioester synthesis, including the original "Boc chemistry" (Boc=tert-butyloxycarbonyl) method (See, for example, (1) Canne, L. E.; Walker, S. M.; Kent, S. B. H. "A General Method for the Synthesis of Thioester Resin Linkers for Use in the Solid-Phase Synthesis of Peptide Alpha-Thioacids." *Tetrahedron Lett.* 1995, 36, 1217-1220; and (2) Hojo, H.; Aimoto, S. "Polypeptide Synthesis Using the S-Alkyl Thioester of a Partially Protected Peptide Segment—Synthesis of the DNA-Binding Domain of C-Myb Protein (142-193)-NH2." *Bull. Chem. Soc. Jpn.* 1991, 64, 111-117) and several Fmoc-compatible systems (See, for example, (1) Shin, Y.; Winans, K. A.; Backes, B. J.; Kent, S. B. H.; Ellman, J. A.; Bertozzi, C. R. "Fmoc-based synthesis of peptide-(alpha)thioesters: Application to the total chemical synthesis of a glycoprotein by native chemical ligation." *J. Am. Chem. Soc.* 1999, 121, 11684-11689; (2) Ingenito, R.; Bianchi, E.; Fattori, D.; Pessi, A. "Solid phase synthesis of peptide C-terminal thioesters by Fmoc/t-Bu chemistry." *J. Am. Chem. Soc.* 1999, 121, 11369-11374; (3) Li, X. Q.; Kawakami, T.; Aimoto, S. "Direct preparation of peptide thioesters using an Fmoc solidphase method." *Tetrahedron Lett.* 1998, 39, 8669-8672; (4) Clippingdale, A. B.; Barrow, C. J.; Wade, J. D. "Peptide thioester preparation by Fmoc solid phase peptide synthesis for use in native chemical ligation." *J. Pept. Sci.* 2000, 6, 225-234; and (5) Bu, X. Z.; Xie, G. Y.; Law, C. W.; Guo, Z. H. "An improved deblocking agent for direct Fmoc solidphase synthesis of peptide thioesters." *Tetrahedron Lett.* 2002, 43, 2419-2422). In ceratin embodiments, the model thioester is a C-terminal glycine thioester, which is locally achiral and cannot be epimerized, and is therefore easy to synthesize. Though the desired GP120 thioester contains an epimerization-prone C-terminal histidine (His) residue, such thioesters have been synthesized previously and have in fact been shown to modulate favorably the rate of NCL (See, for example, Hackeng, T. M.; Griffin, J. H.; Dawson, P. E. "Protein synthesis by native chemical ligation: Expanded scope by using straightforward methodology." *Proc. Natl. Acad. Sci. U.S.A.* 1999, 96, 10068-10073).

It is understood that, although the discussion above regarding Native Chemical Ligation focuses on the preparation of multiglycosylated peptides, the method may readily be adapted to other polyfunctionalized peptides and/or proteins. For example, peptides and/or proteins functionalized at more than one amino acid site with a pharmaceutically useful group or entity may be prepared by the method of the invention.

Equivalents

The representative examples which follow are intended to help illustrate the invention, and are not intended to, nor should they be construed to, limit the scope of the invention. Indeed, various modifications of the invention and many further embodiments thereof, in addition to those shown and described herein, will become apparent to those skilled in the art from the full contents of this document, including the examples which follow and the references to the scientific and patent literature cited herein. In but one illustrative example, protecting groups play an important role in the synthesis of the carbohydrate domains and synthetic conjugates, as described herein; however it will be appreciated by one of ordinary skill in the art that the present invention encompasses the use of various alternate protecting groups known in the art. Those protecting groups used in the disclosure including the Examples below are merely illustrative.

It should further be appreciated that, uless otherwise indicated, the contents of those cited references are incorporated herein by reference to help illustrate the state of the art. The following examples contain important additional information, exemplification and guidance which can be adapted to the practice of this invention in its various embodiments and the equivalents thereof.

Exemplification

The method of this invention can be understood further by the examples that illustrate some of the processes by which the inventive method may be practice. It will be appreciated, however, that these examples do not limit the invention. Variations of the invention, now known or further developed, are considered to fall within the scope of the present invention as described herein and as hereinafter claimed.

1) General Description of Synthetic Methods:

The practitioner has a well-established literature of peptide, protein and glycoside chemistry to draw upon, in combination with the information contained herein, for guidance on synthetic strategies, protecting groups, and other materials and methods useful for practicing the method of this invention.

The various references cited herein provide helpful background information on preparing complex glycosides, glycosylated peptides and other glycosylated constructs that may be applied and/or adapted to the method of the present invention.

According to the present invention, any available techniques can be used to practice the method of the invention. For example, a variety of solution phase synthetic methods such as those discussed in detail below may be used. Alternatively or additionally, a variety combinatorial techniques, parallel synthesis and/or solid phase synthetic methods known in the art may be used.

Starting materials and reagents used in practicing the specific embodiments of the invention detailed below and herein are either available from commercial suppliers such as Aldrich Chemical Company (Milwaukee, Wis.), Bachem (Torrance, Calif.), Sigma (St. Louis, Mo.), or are prepared by methods well known to a person of ordinary skill in the art following procedures described in such references as Fieser and Fieser 1991, "Reagents for Organic Synthesis", vols 1-17, John Wiley and Sons, New York, N.Y., 1991; Rodd 1989 "Chemistry of Carbon Compounds", vols. 1-5 and supps, Elsevier Science Publishers, 1989; "Organic Reactions", vols 1-40, John Wiley and Sons, New York, N.Y., 1991; March 2001, "Advanced Organic Chemistry", 5th ed. John Wiley and Sons, New York, N.Y.; and Larock 1990, "Comprehensive Organic Transformations: A Guide to Functional Group Preparations", $2^{nd}$ ed. VCH Publishers. These schemes are merely illustrative of some embodiments of the present invention, and various modifications to these schemes can be made and will be suggested to a person of ordinary skill in the art having regard to this disclosure.

In practicing the invention, starting materials, intermediates, and compounds may be isolated and purified using conventional techniques, including filtration, distillation, crystallization, chromatography, and the like. They may be characterized using conventional methods, including physical constants and spectral data.

Methods for preparing glycopeptides (e.g., O- or N-linked glycopeptides) and for conjugating peptides and glycopeptides to carriers are known in the art. For example, guidance may be found in U.S. Pat. No.: 6,660,714; U.S. patent application Ser. Nos.: 09/641,742; 10/209,618; and 10/728,041; U.S. Provisional Patent Application Nos.: 60/500,161 and 60/500,708; and International Patent Application Nos.: PCT/US03/38453 and PCT/US03/38471; each of the above-referenced patent documents are hereby incorporated by reference herein.

Overview

Following extensive earlier studies, wherein our chemistry was interfaced with important findings from other laboratories,[12] we demonstrated the ability to ligate fully synthetic N-linked glycopeptides containing various complex oligosaccharides to larger polypeptide domains.[13] For example, major glycosylated subsections of prostate specific antigen (PSA)[3a] and gp120[14] could be obtained. Provided herein is an exemplary convergent approach to access polypeptides multiply glycosylated at designated sites.[15] As discussed previously, glycoproteins have potentially important clinical roles in the contexts of vaccines,[2] diagnostics,[3] and therapeutics.[4] The method of the present invention thus has important applications in the field of medicine since it offers access to complex therapeutically useful glycoproteins.

Scheme 7 schematizes an embodiment of the present invention. For example, glycopeptides 4 and 7 may be generated in a convergent way from their respective glycan and peptide precursors, and may be coupled with full convergence to reach 8.

perhaps be interdicted by the machinery appropriate to native chemical ligation (NCL),[12c] ultimately culminating in 8.

While the proposal for the intermediacy of a discreet thioester 14 is certainly attractive, it is not necessarily an obligatory event en route to ligation. Thus, as suggested in structure 13, the presence of a free ortho-benzene thiol function might well enhance the acylating facility of the phenolic

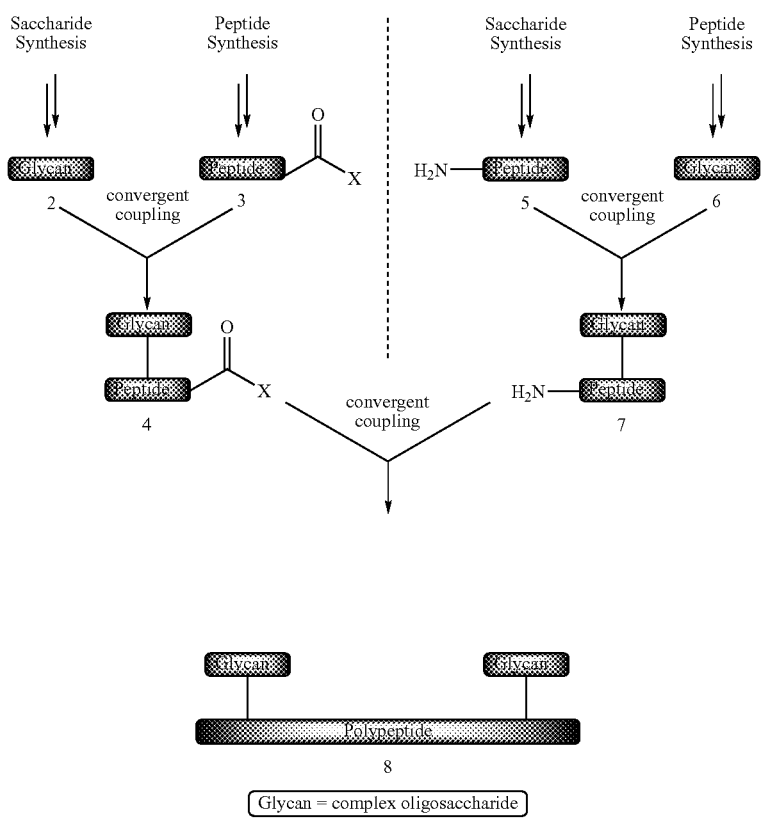

Scheme 7.
A convergent synthesis of bifunctional glycopeptides.

Glycan = complex oligosaccharide

In one embodiment, the synthesis of a suitable glycopeptide acyl donor for ligation with 7 was investigated. One approach was based on utilizing building block 4, in the form of a thioester, as acyl donor. However, the preparation of a thioester such as 4 by convergent means[16] appeared to present difficulties.

It was in pondering this problem that an attractive possibility presented itself (Scheme 8). The synthesis of a phenolic ester equipped with an unsymmetrical disulfide (cf. 10) was then investigated. The phenolic ester linkage would in itself probably not manifest sufficient reactivity to serve as a viable acylating agent. However, equipped as it would be with an ortho-disulfide moiety, the phenolic ester could operate as an incipient acyl donor. Thus, reduction of the disulfide in 12, as shown, might well set the stage for in situ elaboration into a thioester (cf. 13→14) by O→S acyl migration. Thioester 14, present in an unfavorable, but dynamic equilibrium, could ester,[17] perhaps through in situ hydrogen bonding or anchimeric assistance. In either case, the sequence is set into motion only upon reductive cleavage of the disulfide.

The synthesis of the masked glycopeptide acyl donor was accomplished as follows (Scheme 8). Commercially available 2-mercaptophenol (9) was oxidized to its symmetrical disulfide. Subsequent exchange with excess ethyl disulfide[18] furnished an unsymmetrical, aryl-alkyl disulfide. Acylation of the phenolic hydroxyl group with Boc-phenylalanine followed by acidic cleavage of the Boc protecting group afforded phenylalanine derivative 10. Standard peptide coupling of 10 with a fully protected peptide acid[19] followed by global deprotection provided 11,[20] which contains a free aspartate residue. Aspartylation of a chitobiose-derived glycosylamine with 11 afforded the virtual acyl donor 12, corresponding to our target structure 4 (Scheme 7).

Scheme 8.
A structure, synthesis, and proposed mechanism of a masked glycopeptide acyl donor.[a]

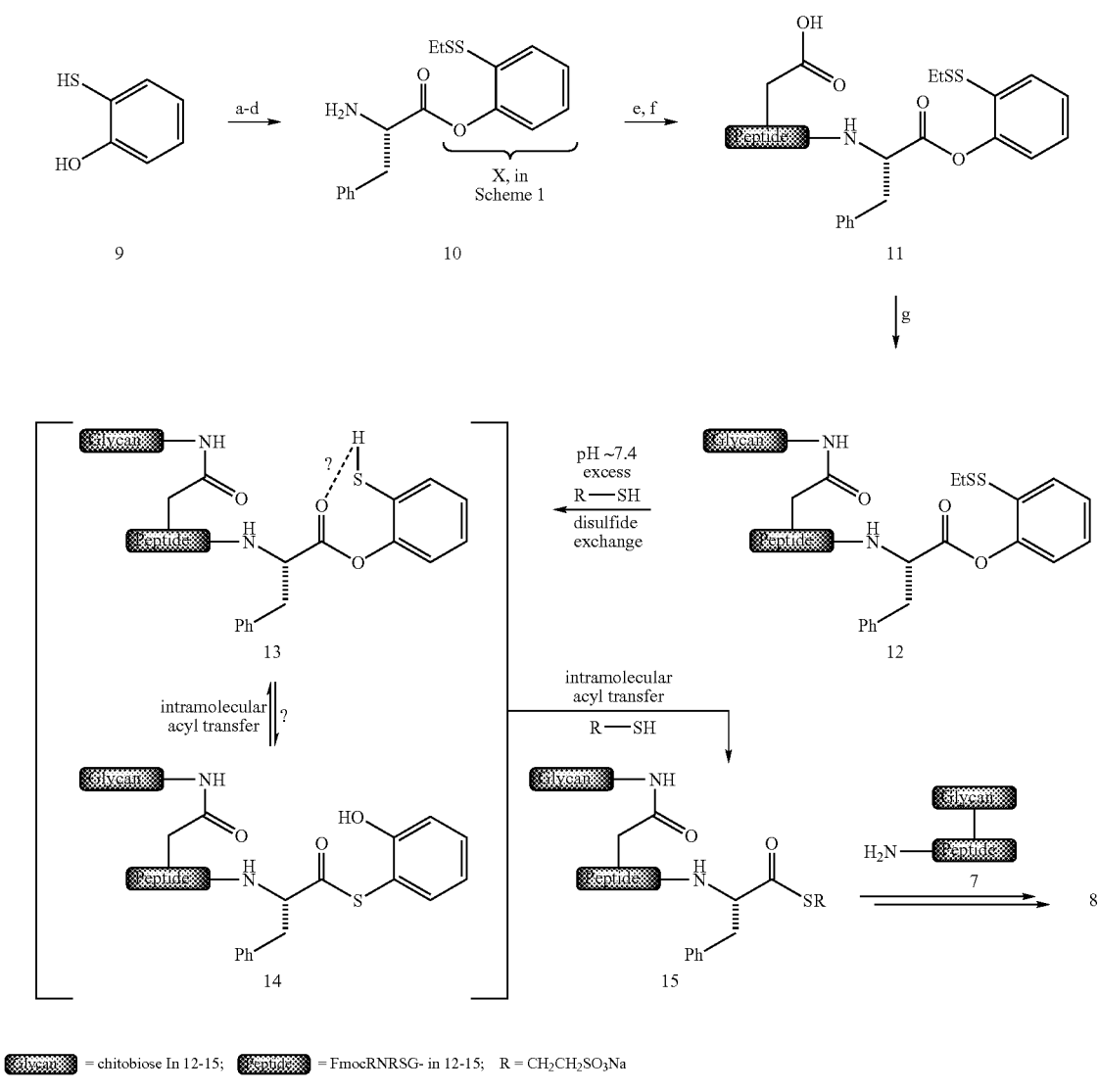

= chitobiose In 12-15;   = FmocRNRSG- in 12-15;   R = CH$_2$CH$_2$SO$_3$Na

[a]Reagents and conditions:
a I$_2$, MeOH, H$_2$O;
b BF$_3$·OEt$_2$, EtSSEt, CH$_2$Cl$_2$, 99%, 2 steps;
c Boc-Phe-OH, EDCI, DMAP, CH$_2$Cl$_2$/THF, 93%;
d 4N HCl/dioxane, 94%;
e Fmoc-Arg(Pbf)-Asp($^t$Bu)-Arg(Pbf)-Ser($^t$Bu)-Gly-OH, HATU, DIEA, DMF, 61%;
f TFA:phenol:Et$_3$SiH:H$_2$O 35:2:1:1, 60%
g GlcNAcβ1→4GlcNAcβ-NH$_2$, HATU, DIEA, DMSO, 52%.

As a preliminary probe of the practicability of this scheme, henylalanine derivative 10 was subjected to the neutral, aqueous, reducing reaction conditions described above, along with free cysteine (Scheme 9). The desired free dipeptide Phe-Cys (17) was obtained in 78% isolated yield. Only a single product was observed by LCMS and $^1$H NMR, strongly suggesting that epimerization at the α-carbon of phenylalanine did not occur.

Scheme 9.
An example of the latent acyl donor function.

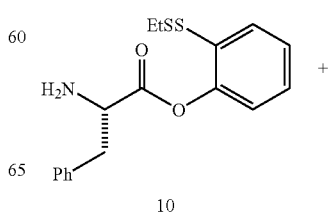

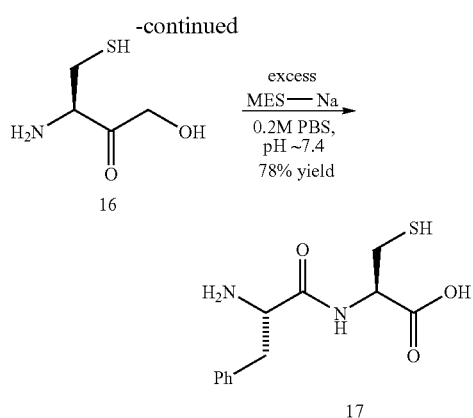

The synthesis of bifunctional glycopeptides was then carried out. Thus, 12 was treated with excess sodium 2-mercaptoethanesulfonate (MES-Na) at neutral pH in aqueous phosphate buffered saline (PBS) in the presence of 18,[21] containing a latent N-terminal cysteine residue (Scheme 10). As observed by LCMS during the reaction, 12 was almost instantaneously (less than 3 min) converted to the thioester derived from MES-Na (cf. 15); very little hydrolysis to the free carboxylic acid was noted. Over the course of the next several hours, we observed a gradual decrease in the amount of this thioester, with a concomitant increase in the desired product 19. Only one compound of the appropriate mass was observed by LCMS and $^1$H NMR, again indicating a lack of epimerization.

With this proof of principle in hand, attention was directed to investigating the generality of the method. For example, applicability of the method to incorporation of O-linked domains[22] was established, as shown through the synthesis of 20. Notably, the histidine-containing system 21 was also assembled (for structure of 21 and 20, see FIG. 1). Since activated C-terminal histidine residues are known to be particularly susceptible to epimerization,[23] a prophylactic dinitrophenyl (DNP) protecting group[24] was used for the imidazole τ-nitrogen during the synthesis. As expected, the DNP group was cleaved concurrently during the mildly nucleophilic coupling reaction. No indications of epimerization were observed by LCMS or $^1$H NMR.

Figure 2:
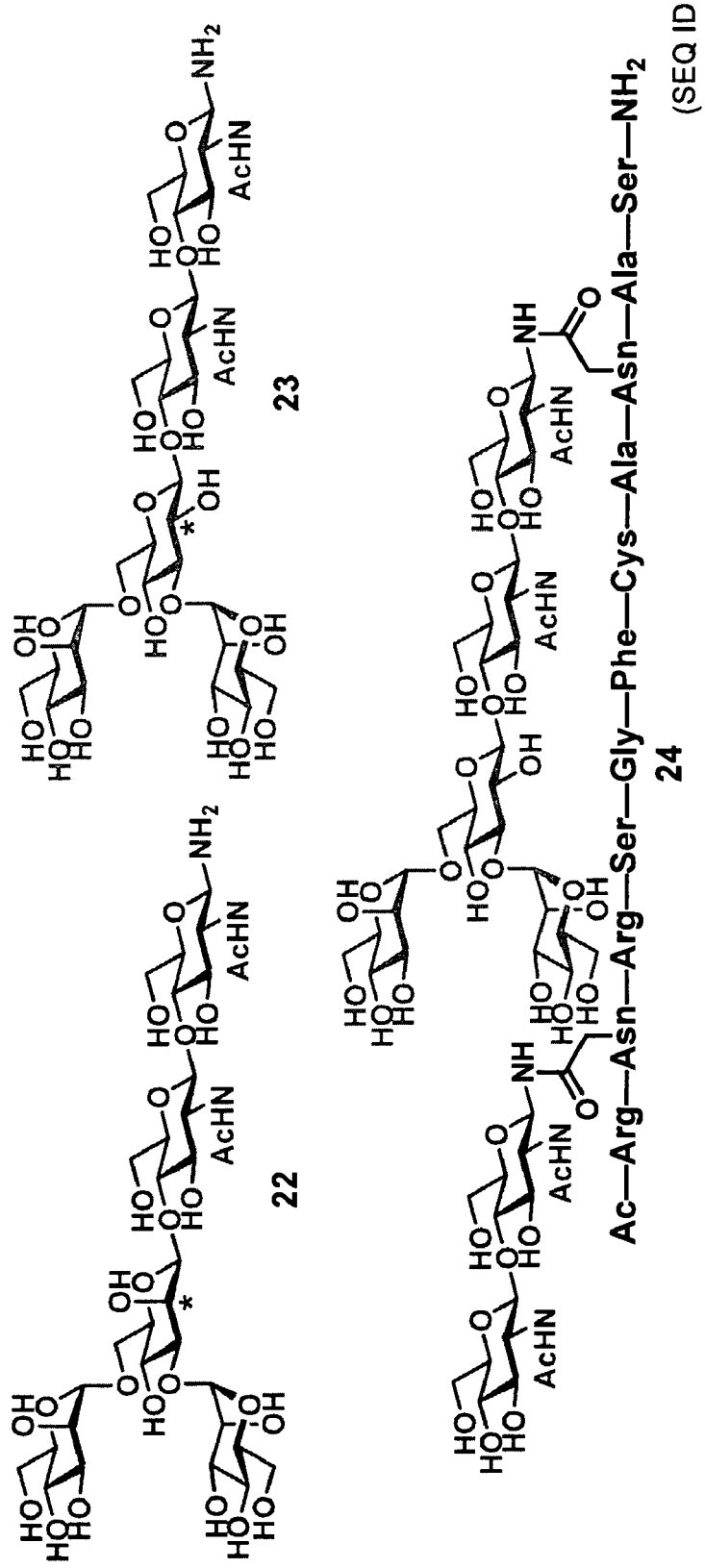
FIG. 2 depicts anomeric β-glycosylamines (22 and 23) that differ at a single stereocenter (asterisks), and a bifunctional glycopeptide (24) containing one of these structurally complex glycans.

Validation of the highly convergent methodology in the context of complex glycans was then investigated. Syntheses of glycosylamines 22[13] and 23[25] (FIG. 2) have been reported previously. It will be noted that these compounds differ in a single stereogenic locus in the interior C-ring (see asterisks). Thus 22 corresponds to a fully stereochemically competent N-linked high mannose oligosaccharide. In contrast, its C-ring C-2 epimer is an unnatural stereochemical mutant. Studies aimed at evaluating whether high-mannose binding lectins can discriminate between point mutants that differ in only one out of a total of 25 stereochemical loci are underway.

Preparation of pentasaccharide-derived glycopeptide coupling partners proceeded via Lansbury aspartylation[12b] of 22 and 23 with 25 and 26, which afforded 27 and 28, respectively. Coupling of 28 with a relatively simple chitobiose-containing acyl donor gave 24 (FIG. 2) in 77% yield.

Scheme 10.
Exemplary convergent coupling or functionalized glycopeptides.

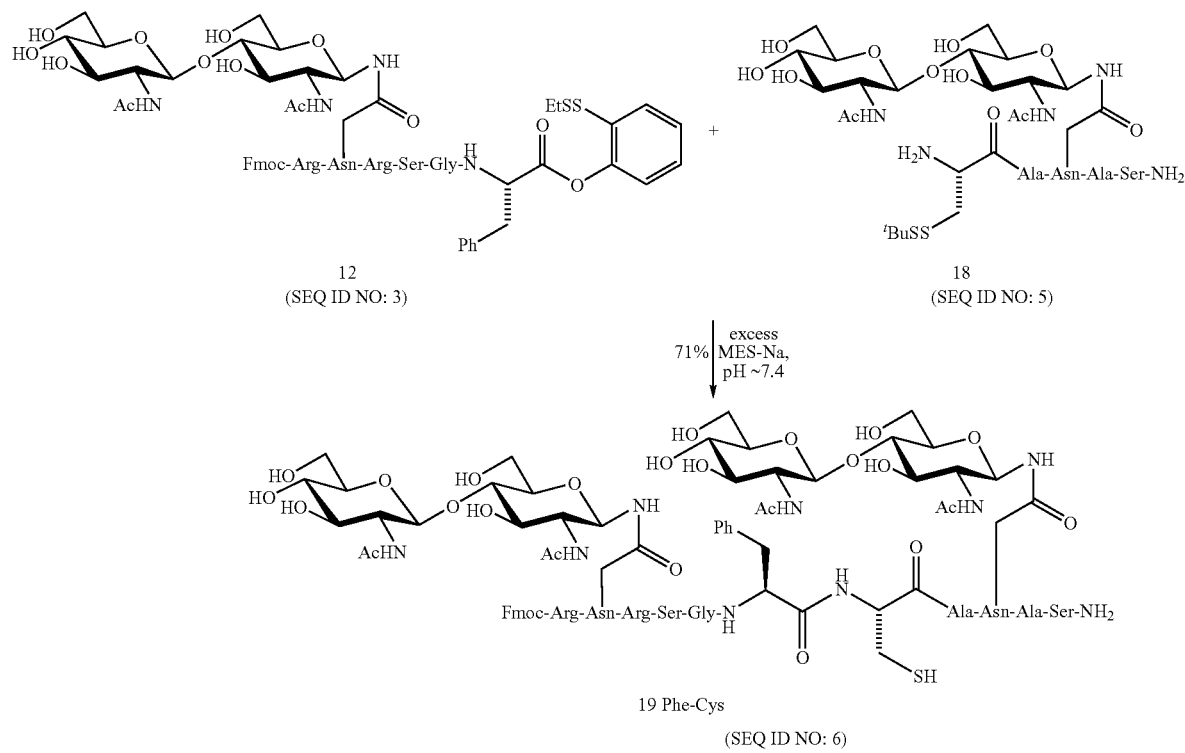

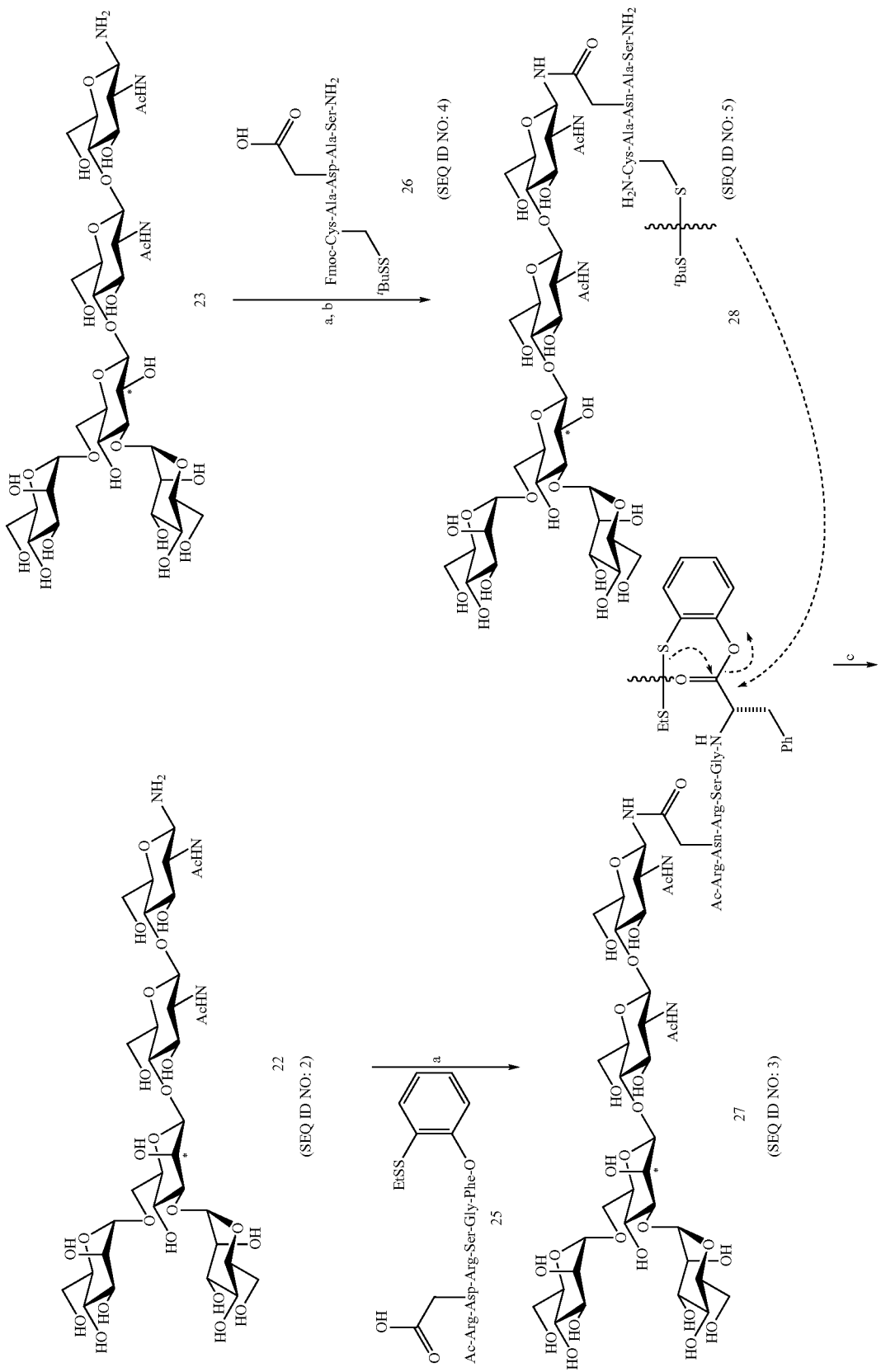

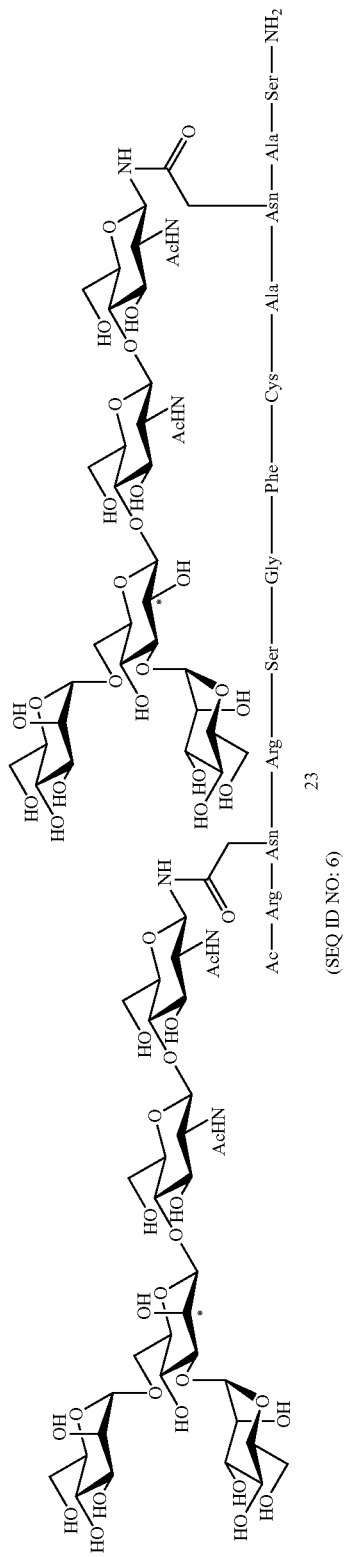
(SEQ ID NO: 6)
*Reagents and conditions:
a 25 or 26, HATU, DIEA, DMSO, 50% for 27 (from 22), 71% for 28 (from 23);
b 20% piperidine in DMF, 63%;
c 0.2M phosphate, 0.2M NaCl, pH ~7.4, excess MES-Na, 75%.

Coupling of 27 and 28 was accomplished smoothly upon reductive cleavage of the disulfide linkage in 27, affording 29 as shown in Scheme 11. Aside from validating the methodology in a striking way, the synthesis of 29 serves to pinpoint the power of the total synthesis approach: Since one of its carbohydrates is unnatural, 29 cannot readily be obtained from natural sources or via enzymatic manipulations.

In summary, a convergent method for the synthesis of diglycosylated peptides is described herein. The mechanistic rationale set forth in Scheme 8 is supported by the identification of the MES-Na thioester as a reaction intermediate. Furthermore, potential hydrolysis and C-terminal epimerization of the glycopeptide acyl donor have been suppressed. It seems likely that the method and logic set forth above will enjoy application in the building of complex glycopeptides of biological and even medicinal consequence.

It will be appreciated that the method can readily be applied to the preparation of multi-glycosylated peptides (e.g., comprising more than two non-adjacent glycosides covalently linked at designated sites).

General Reaction Procedures:

Unless mentioned specifically, reaction mixtures were stirred using a magnetically driven stirrer bar. Reactions involving air or moisture-sensitive reagents or intermediates were performed under argon or nitrogen atmosphere in glassware which had been heat gun or flame-dried under high vacuum. An inert atmosphere refers to either dry argon or dry nitrogen. Reactions were monitored either by thin layer chromatography, by proton nuclear magnetic resonance (NMR) or by high-pressure liquid chromatography (HPLC), of a suitably worked up sample of the reaction mixture.

Indicated reaction temperatures refer to those of the reaction bath, while room temperature (rt) is noted as 22° C. Preparative reactions were stirred magnetically. Tetrahydrofuran (THF), diethyl ether ($Et_2O$), methylene chloride ($CH_2Cl_2$), and toluene were obtained from a dry solvent system (activated alumina columns, positive pressure of argon). All other solvents were used as received in Sure/Seal bottles (Aldrich). Triethylamine ($Et_3N$), diisopropylethylamine (i-$Pr_2NEt$), pyridine, and 2,6-lutidine were distilled from $CaH_2$ immediately prior to use. All other reagents were purchased from Aldrich at the highest commercial quality and used without further purification.

General Work up Procedures:

Unless mentioned specifically, reaction mixtures were cooled to room temperature or below then quenched, when necessary, with either water or a saturated aqueous solution of ammonium chloride. Desired products were extracted by partitioning between water and a suitable water-immiscible solvent (e.g. ethyl acetate, dichloromethane, diethyl ether). The desired product containing extracts were washed appropriately with water followed by a saturated solution of brine. On occasions where the product containing extract was deemed to contain residual oxidants, the extract was washed with a 10% solution of sodium sulphite in saturated aqueous sodium bicarbonate solution, prior to the aforementioned washing procedure. On occasions where the product containing extract was deemed to contain residual acids, the extract was washed with saturated aqueous sodium bicarbonate solution, prior to the aforementioned washing procedure (except in those cases where the desired product itself had acidic character). On occasions where the product containing extract was deemed to contain residual bases, the extract was washed with 10% aqueous citric acid solution, prior to the aforementioned washing procedure (except in those cases where the desired product itself had basic character). Post washing, the desired product containing extracts were dried over anhydrous magnesium sulphate, and then filtered. The crude products were then isolated by removal of solvent(s) by rotary evaporation under reduced pressure, at an appropriate temperature (generally less than 45° C.).

General Purification Procedures:

Unless mentioned specifically, chromatographic purification refers to flash column chromatography on silica, using a single solvent or mixed solvent as eluent. Suitably purified desired product containing elutes were combined and concentrated under reduced pressure at an appropriate temperature (generally less than 45° C.) to constant mass. Final compounds were dissolved in 50% aqueous acetonitrile, filtered and transferred to vials, then freeze-dried under high vacuum before submission for biological testing.

Analytical Equipment:

HPLC: All separations involved a mobile phase of 0.05% TFA (v/v) in water (solvent A)/0.0425% TFA in acetonitrile (solvent B). Preparative, semipreparative, and analytical HPLC separations were performed using a Rainin HXPL solvent delivery system equipped with a Rainin UV-1 detector and one of the following Dynamax-60 Å C. 18 axial compression columns 250 mm in length equipped with a similarly packed guard column: 41.4 mm diameter (prep), 21.4 m diameter (semiprep), or 4.6 mm diameter (analytical). Separations were performed at flow rates of 48 mL/min (prep), 16 mL/min (semiprep), or 1 mL/min (analytical), and were monitored at a wavelength between 214 and 230 nm, depending on column loading. LCMS chromatographic separations were performed using a Waters 2695 Separations Module and a Waters 996 Photodiode Array Detector equipped with a Varian Microsorb C18 2×150 mm column at a flow rate of 0.2 mL/min.

ESMS and LCMS: Electrospray mass spectroscopy and LCMS analyses were obtained on a Waters Micromass ZQ mass spectrometer in conjunction with the Waters HPLC apparatus described above.

NMR: $^1H$ and $^{13}C$ NMR spectra were recorded on Bruker instruments in $CDCl_3$, $CD_3OD$ or $D_2O$ at 400 or 500 MHz for $^1H$ and 100 or 125 MHz for $^{13}C$.

Reagents: All commercial materials were used as received unless otherwise noted. The following solvents were obtained from a dry solvent system and used without further purification: THF, diethyl ether, toluene, and DCM. Reagents were obtained from Aldrich or as noted, with the following exceptions: amino acids and resins for solid phase peptide synthesis were purchased from NovaBiochem; Biosynthesis grade DMF from EM Science; and all other solvents from Fisher Scientific (HPLC grade).

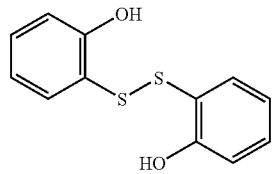

To a stirred, biphasic solution of 2-mercaptophenol (1.0 g, 7.9 mmol) in $H_2O$ (5.1 mL) was added, drop wise, a solution of iodine (1.0 g 4.0 mmol) in methanol (3.5 mL). When the brown iodine color persisted the solution was diluted with ethyl acetate and water. The aqueous layer was removed and extracted with an additional portion of ethyl acetate. The combined organic layers were dried and washed with brine then dried ($Na_2SO_4$) and concentrated to give a brown oil which was used without purification (1.5 g). The product still contains iodine. $^1$H NMR (CDCl$_3$, 500 MHz): δ 7.33-7.37 (m, 2H), 7.22-7.24 (m, 2H), 6.99-7.01 (m, 2H), 6.82-6.85 (m, 2H), 6.22 (brs, 2H). $^1$H NMR (CDCl$_3$, 400 MHz): δ 7.35 (dt, J=8.16, 1.65 Hz, 2H), 7.22 (dd, J=7.52, 1.65 Hz, 2H), 7.00 (dd, J=8.16, 1.15 Hz, 2H), 6.83 (dt, J=7.52, 1.15 Hz, 2H), 6.22 (s, 2H) $^{13}$C NMR (CDCl$_3$, 125 MHz): δ 157.3, 136.6, 133.6, 121.4, 120.3, 116.1. ESI-MS: Calcd. for C$_{12}$H$_{10}$O$_2$S$_2$ [M+NH$_4$]$^+$ 267.8. Found: 267.8.

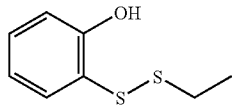

To a stirred solution of the disulfide (1.5 g crude, ~4mmol) in CH$_2$Cl$_2$ (25 mL) was added ethyldisulfide (10.5 mL, 79.9 mmol) and then BF$_3$.OEt$_2$ (10.1 mL, 79.9 mmol). The reaction was stirred at room temperature for three hours and then carefully quenched by the addition of (aq.) NaHCO$_3$. The organic layer was drained and the aqueous layer was extracted with an additional portion of CH$_2$Cl$_2$. The combined organic layers were dried (MgSO$_4$) and concentrated to give a yellow oil. Purification by silica gel chromatography (20% ethyl acetate in hexane) gave the desired product as a clear, slightly yellow oil (1.45 g, 99%). $^1$H NMR (CDCl$_3$, 500 MHz): δ 7.48-7.51 (m, 1H), 7.28-7.32 (m, 1H), 6.99-7.01 (m, 1H), 6.86-6.9 (m, 1H), 6.34 (brs, 1H), 2.78 (q, J=7.4 Hz, 2H), 1.35 (t, J=7.4 Hz, 3H). $^{13}$C NMR (CDCl$_3$, 125 MHz): δ 156.9, 135.2, 132.2, 121.0, 116.2, 32.4, 14.1. ESI-MS: Calcd. for C$_8$H$_{10}$OS$_2$ [M+Na]$^+$ 208.8. Found: 208.8.

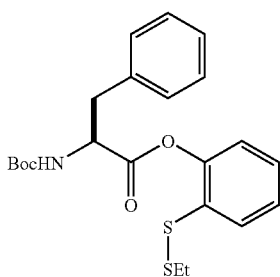

To a solution of the phenol (1.45 g, 8 mmol) and Boc-Phe-OH (2.65 g, 10 mmol) in CH$_2$Cl$_2$ (25 mL) and THF (5 mL) was added EDCI (1.92 g, 10 mmol) and DMAP (98 mg, 0.8 mmol). The resulting solution was stirred at room temperature for 18 hr at which point the volatile materials were removed in vacuo. The resulting oil was taken up in EtOAc and washed with 1N HCl, H$_2$O, and then brine. The organic layer was dried (Na$_2$SO$_4$) and concentrated to give a slightly yellow oil. Purification by silica gel chromatography (30% ethyl acetate in hexane) gave a clear, colorless oil (3.5 g, >99%). $^1$H NMR (CDCl$_3$, 400 MHz): δ 7.78-7.81 (m 1H), 7.23-7.36 (m, 7H), 7.01-7.03. (m, 1H), 5.02 (d, J=8.16 Hz, 1H), 4.86-4.91 (m, 1H), 3.31 (abx, J$_{ab}$=13.98 Hz, J$_{ax}$=5.41 Hz, J$_{bx}$=7.22 Hz, 2H), 2.72 (q, J=7.33 Hz, 2H), 1.42 (s, 9H), 1.29 (t, J=7.33 Hz, 3H). ESI-MS: Calcd. for C$_{22}$H$_{27}$NO$_4$S$_2$ [M+Na]$^+$ 456.0. Found: 456.0.

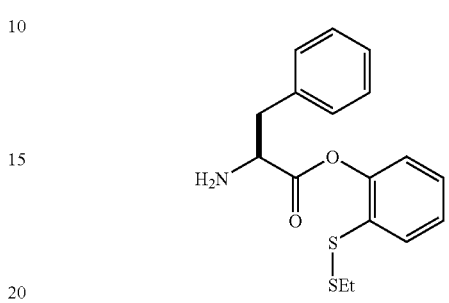

To a 250 mL round-bottomed flask equipped with a magnetic stir bar was added the above phenylalanine derivative (3.0 g, 6.9 mmol) as well as a 4M solution of HCl in dioxane (86 mL, 345 mmol) and the reaction was stirred under argon at room temperature for 1.5 hr. At that point the reaction was concentrated in vacuo, leaving a white solid. This material was triturated with ether and subsequently concentrated. This process was repeated (3×) leaving the crude product as a white solid. The material was dissolved in 30% B, shell frozen and lyophilized to give a white powder (2.17 g, 94%). $^1$H NMR (CD$_3$OD, 400 MHz): δ 7.93-7.95 (m, 1H), 7.52-7.42 (m, 7H), 7.23-7.21 (m, 1H), 4.81 (dd, J=8.35, 5.73 Hz, 1H), 3.56 (abx, J$_{ab}$=14.48 Hz, J$_{ax}$=5.73 Hz, J$_{bx}$=8.35 Hz, 2H), 2.85 (q, J=7.34 Hz, 2H), 1.37 (t, J=7.34 Hz, 3H). $^{13}$C NMR (CDCl$_3$, 125 MHz): δ 169.0, 149.4, 135.6, 131.9, 131.3, 131.0, 130.7, 129.9, 129.6, 129.1, 123.9, 55.6, 38.0, 34.1, 14.9. ESI-MS: Calcd. for Cl$_7$H$_{19}$NO$_2$S$_2$ [M+H]$^+$ 334.1. Found: 334.2.

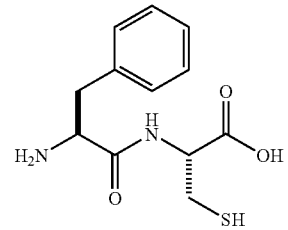

The phenylalanine derivative 10 (15 mg, 45 µmol) and L-cysteine (6 mg, 49 µmol) were placed into a LCMS vial along with a flea-sized stirbar. In a second vial were mixed MES—Na (25 mg, 150 µmol) and phosphate buffered saline (PBS) (0.2M NaCl, 0.2M phosphate, pH=7.5, 2 mL). The MES-Na solution was then added directly to the amino acids, and the reaction was monitored by LCMS. After two hours the reaction appeared to be complete and TCEP (129 mg, 450

μmol) was added. This was stirred for 1 hour and then injected directly onto the HPLC for purification. The desired compound was obtained as a white powder after lyophilization (9.4 mg, 78%). $^1$HNMR (D$_2$O): δ 7.36-7.45 (m, 3H), 7.31-7.33 (m, 2H), 4.63 (dd, J=6.61, 4.83 Hz, 1H), 4.34 (dd, J=7.24, 7.18 Hz, 1H), 3.25 (abx, J$_{ab}$=14.1 Hz, J$_{ax}$=7.18 Hz, J$_{bx}$=7.24 Hz, 2H), 2.96 (abx, J$_{ab}$=14.2 Hz, J$_{ax}$=4.83 Hz, J$_{bx}$=6.61 Hz, 2H). LCMS: 5-65% B over 20 min, rt=8.53 min. HPLC: 5-95% B over 30 min, rt=11.45 min. ESI-MS: Calcd. for C$_{12}$H$_{16}$N$_2$O$_3$S [M+H]$^+$ 269.1., Found: 269.1

Exemplary Ligation Conditions:

The two glycopeptide halves (12, 2.2 mg, 1.44 μmol) (18, 1.4 mg, 1.44 μmol) were placed in a LCMS vial along with a flea-sized stirbar. A stock solution of MESNa (18.3 mg, 111 mmol) in phosphate buffered saline (0.2 M NaCl, 0.2 M phosphate, pH=7.4, 1 mL) was made and of this, 600 μL was added to the glycopeptides. The reaction was monitored by LCMS and, once finished, TCEP (25 mg, 0.087 mmol) was added and the solution stirred for 2 hr then injected directly onto the HPLC for purification.

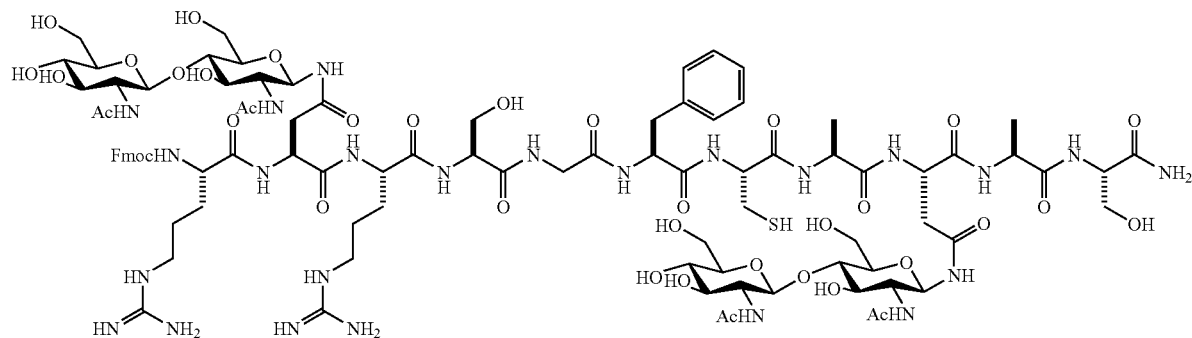

(SEQ ID NO: 6)

LCMS: 5-65% B over 20 min, rt=9.98 min. HPLC: 25-55% B over 30 min, rt=7.65 min. ESI-MS: Calcd. for C$_{93}$H$_{138}$N$_{24}$O$_{37}$S [M+2H]$^{2+}$ 1108.5. Found: 1108.6, [M+3H]$^{3+}$ 739.3. Found: 739.5.

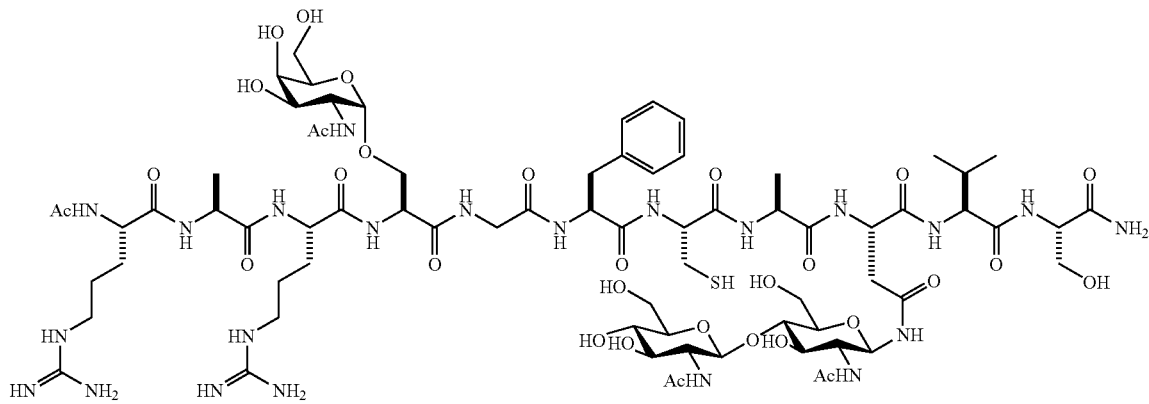

(SEQ ID NO: 7)

LCMS: 5-65% B over 20 min, rt=11.40 min. HPLC: 5-65% B over 20 min, rt=9.85 min. ESI-MS: Calcd. for $C_{73}H_{120}N_{22}O_{30}S$ $[M+2H]^{2+}$ 909.4. Found: 909.5, $[M+3H]^{3+}$ 606.6. Found: 606.8.
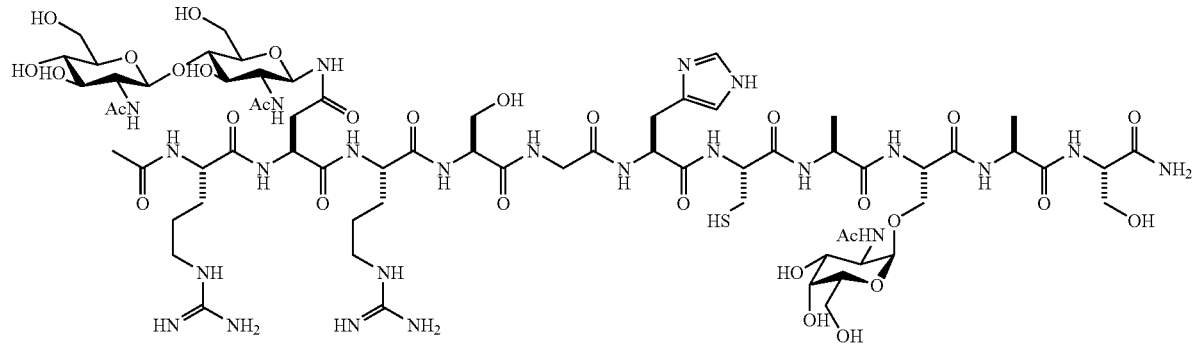
(SEQ ID NO: 8)
LCMS: 5-65% B over 20 min, rt=4.02 min. HPLC: 5-65% B over 20 min, rt=6.71 min. ESI-MS: Calcd. for $C_{73}H_{120}N_{22}O_{30}S$ $[M+2H]^{2+}$ 898.4. Found: 898.6.
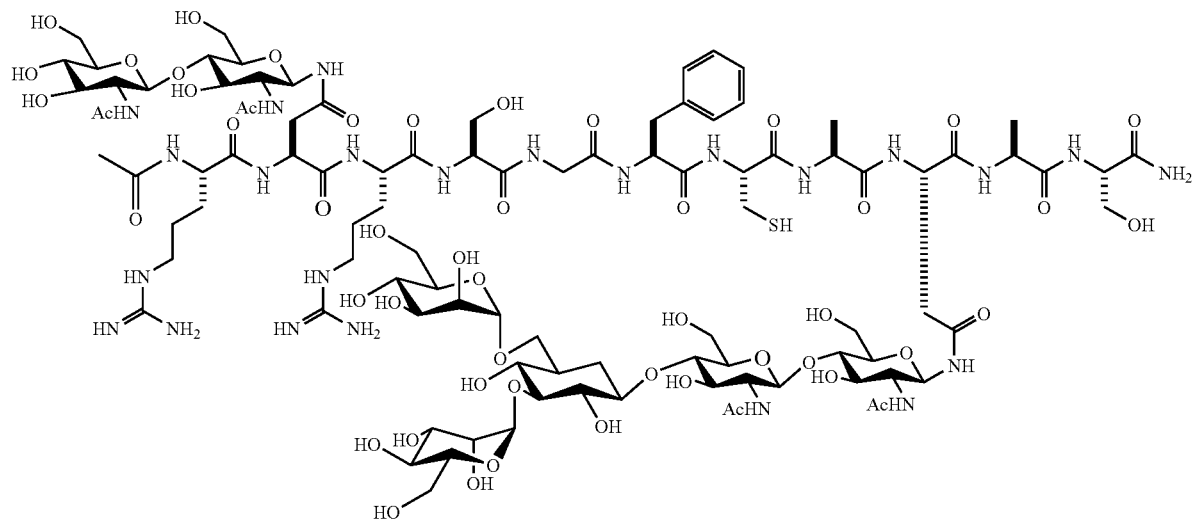
(SEQ ID NO: 6)

LCMS: 5-65% B over 20 min, rt=7.81 min. HPLC: 5-65% B over 20 min, rt=8.39 min. ESI-MS: Calcd. for $C_{98}H_{160}N_{24}O_{51}S$ $[M+2H]^{2+}$ 1261.5. Found: 1261.5, $[M+3H]^{3+}$ 841.4. Found: 841.5.

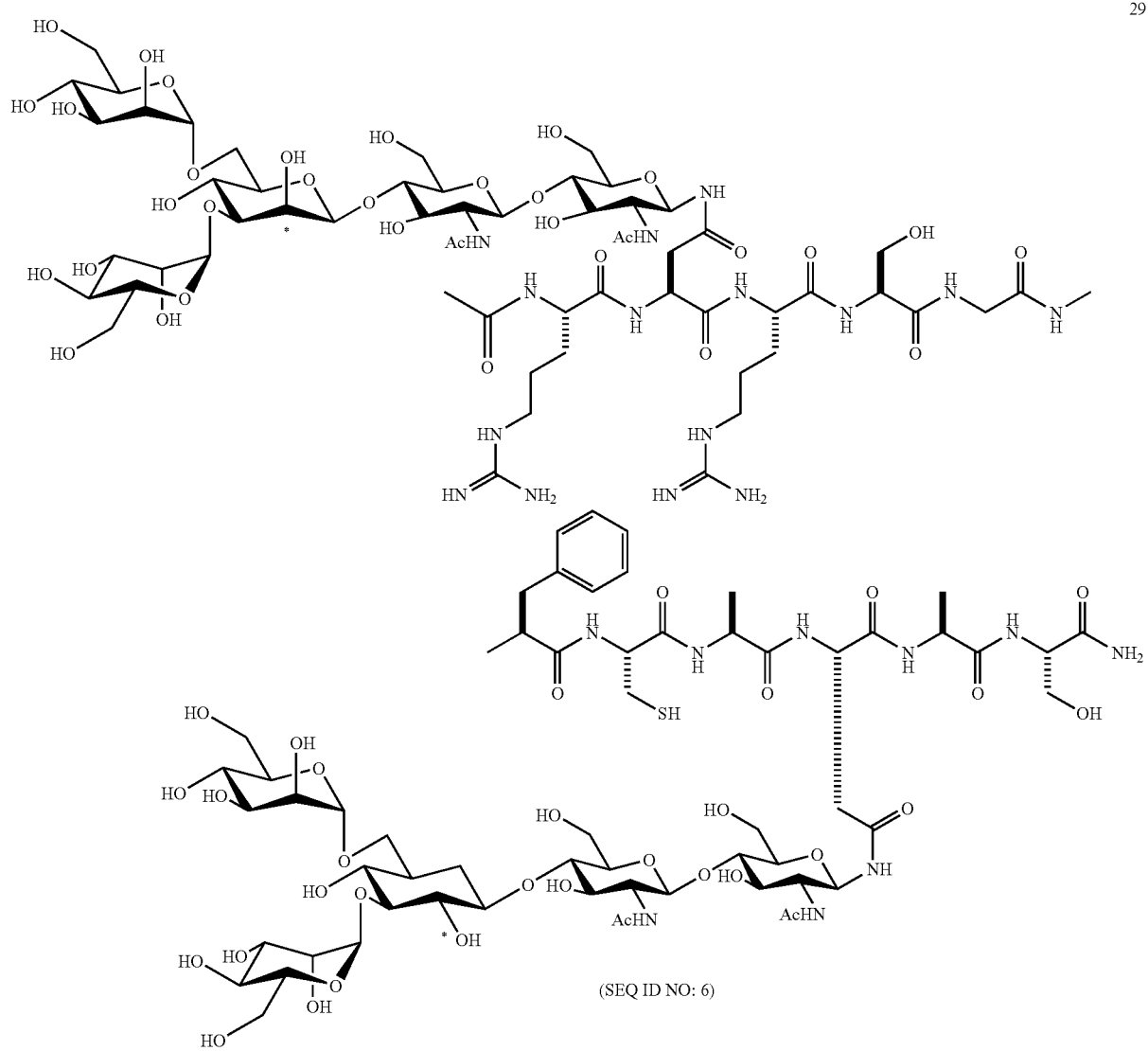

(SEQ ID NO: 6)

LCMS: 5-45% B over 20 min, rt=10.82 min. HPLC: 5-45% B over 20 min. rt=9.31 min. ESI-MS: Calcd. for $C_{98}H_{160}ON_{24}O_{51}S$ $[M+2H]^{2+}$ 1504.6. Found: 1504.9, $[M+3H]^{3+}$ 1003.4. Found: 1003.7.

Abbreviations and Glossary

A: alanine
Ac: acetyl
Ala: alanine
Arg: arginine
Asn: asparagine
Asp: aspartic acid
Bn: benzyl
Boc: tert-butyloxycarbonyl
Bu: butyl
Bz: benzoyl
CAN: ceric ammonium nitrate
C-terminus: peptide carbonyl terminus
Cys: cysteine
D: aspartic acid
DIEA: N,N-diisopropylethylamine
DMAP: N,N-Dimethylaminopyridine
DMF: dimethyl formamide
DMSO: dimethyl sulfoxide
DTBMP: di-tert-butylmethylpyridine
DTBP: di-tert-butylpyridine
Et: ethyl
Fmoc: 9-fluorenylmethyloxycarbonyl
G: glycine
Gal: galactose
Glc: glucose
Gln: glutamine
Glu: glutamic acid
Gly: glycine
H: histidine HATU: 7-azahydroxybenzotriazolyl tetramethyluronium hexafluorophosphate
His: histidine
Ile: isoleucine
K: lysine
kDa: kilodaltons
KLH: keyhole limpet hemocyanin
L: leucine
Leu: leucine
Lys: lysine
Man: mannose
MES-Na: 2-mercaptoethanesulfonic acid, sodium salt
MHC: major histocompatibility complex
N: asparagine
NAc: N-acetyl
NCL: native chemical ligation
N-terminus: peptide amine terminus
O-linked: linked through an ethereal oxygen
Pam3Cys: tripalmitoyl-S-glycerylcysteinylserine
PBS: phosphate-buffered saline
Ph:phenyl
PMB: p-methoxybenzyl
Pro: proline
GP120: prostate specific antigen
Py: pyridine
QS21: a glycosteroidal immunoadjuvant
R: arginine
S: serine
sat. aq.: saturated aqueous
Ser: serine
T: threonine
TBAF:: tetra-n-butylammonium fluoride
TBS: tert-butyldimethylsilyl
tBu: tert-butyl
Tf: trifluoromethanesulfonate
TFA: Trifluoroacetic acid
THF: tetrahydrofuran
Thr: threonine
t-GP120: total prostate specific antigen
Trp: tryptophan
V: valine
Val: valine
W: tryptophan

REFERENCES (1) (a) Imperiali, B.; O'Connor, S. E.; Hendrickson, T.; Kellenberger, C. *Pure Appl. Chem.* 1999, 71, 777-787. (b) Lis, H.; Sharon, N. *Eur. J. Biochem.* 1993, 218, 1-27. (c) Rudd, P. M.; Elliott, T.; Cresswell, P.; Wilson, I. A.; Dwek, R. A. *Science* 2001, 291, 2370-2376. (d) Bertozzi, C. R.; Kiessling, L. L. *Science* 2001, 291, 2357-2364.

(2) (a) Calarese, D. A.; Scanlan, C. N.; Zwick, M. B.; Deechongkit, S.; Mimura, Y.; Kunert, R.; Zhu, P.; Wormald, M. R.; Stanfield, R. L.; Roux, K. H.; Kelly, J. W.; Rudd, P. M.; Dwek, R. A.; Katinger, H.; Burton, D. R.; Wilson, I. A. *Science* 2003, 300, 2065-2071. (b) von Mensdorff-Pouilly, S.; Snijdewint, F. G.; Verstraeten, A. A.; Verheijen, R. H.; Kenemans, P. *Int. J. Biol. Markers* 2000, 15, 343-356.

(3) (a) Dudkin, V. Y.; Miller, J. S.; Danishefsky, S. J. *J. Am. Chem. Soc.* 2004, 126, 736-738. (b) Peracaula, R.; Tabares, G.; Royle, L.; Harvey, D. J.; Dwek, R. A.; Rudd, P. M.; de Llorens, R. *Glycobiology* 2003, 13, 457-470.

(4) (a) Ridley, D. M.; Dawkins, F.; Perlin, E. *J. Natl. Med. Assoc.* 1994, 86, 129-135. (b) Durand, G.; Seta, N. *Clin. Chem.* 2000, 46, 795-805. (c) Koeller, K. M.; Wong, C. H. *Nat. Biotechnol.* 2000, 18, 835-841.

(5) Rush, R. S.; Derby, P. L.; Smith, D. M.; Merry, C.; Rogers, G.; Rohde, M. F.; Katta, V. *Anal. Chem.* 1995, 67, 1442-1452.

(6) Lai, P. H.; Everett, R.; Wang, F. F.; Arakawa, T.; Goldwasser, E. *J. Biol. Chem.* 1986, 261, 3116-3121.

(7) Berman, H. M.; Westbrook, J.; Feng, Z.; Gilliland, G.; Bhat, T. N.; Weissig, H.; Shindyalov, I. N.; Bourne, P. E. *Nucleic Acids Res.* 2000, 28, 235-242.

(8) Cheetham, J. C.; Smith, D. M.; Aoki, K. H.; Stevenson, J. L.; Hoeffel, T. J.; Syed, R. S.; Egrie, J.; Harvey, T. S. *Nat. Struct. Biol.* 1998, 5, 861-866.

(9) Rahbek-Nielsen, H.; Roepstorff, P.; Reischl, H.; Wozny, M.; Koll, H.; Haselbeck, A. *J. Mass Spectrom.* 1997, 32, 948-958.

(10) (a) Kornfeld, R.; Kornfeld, S. *Annu. Rev. Biochem.* 1985, 54, 631-664. (b) Roth, J. *Chem. Rev.* 2002, 102, 285-303.

(11) Geyer, H.; Holschbach, C.; Hunsmann, G.; Schneider, J. *J. Biol. Chem.* 1988, 263, 11760-11767.

(12) (a) Likhosherstov, L. M.; Novikova, O. S.; Derevitskaja, V. A.; Kochetkov, N. K. *Carbohydr. Res.* 1986, 146, C1-C5. (b) Cohen-Anisfeld, S. T.; Lansbury, P. T. *J. Am. Chem. Soc.* 1993, 115, 10531-10537. (c) Dawson, P. E.; Muir, T. W.; Clark-Lewis, I.; Kent, S. B. H. *Science* 1994, 266, 776-779.

(13) Miller, J. S.; Dudkin, V. Y.; Lyon, G. J.; Muir, T. W.; Danishefsky, S. J. *Angew. Chem. Int. Ed.* 2003, 42, 431-434.

(14) Manuscript submitted.

(15) For the state of the art in biological approaches toward multiply glycosylated proteins, see: Zhang, Z.; Gildersleeve, J.; Yang, Y. Y.; Xu, R.; Loo, J. A.; Uryu, S.; Wong, C. H.; Schultz, P. G. *Science* 2004, 303, 371-373.

(16) Significant advances in this type of problem arose through the use of Ellman's Fmoc-based sulfonamide linker (Shin, Y.; Winans, K. A.; Backes, B. J.; Kent, S. B. H.; Ellman, J. A.; Bertozzi, C. R. *J. Am. Chem. Soc.* 1999, 121, 11684-11689), which has been employed in the synthesis of glycopeptide thioesters. In certain embodiments of the method we practice here, however, maximal convergence is emphasized, as opposed to a "cassette" approach to glycan incorporation. We note that certain glycosidic linkages (e.g., fucosidic linkages in erythropoietin) are particularly unstable toward the acidic conditions (TFA) typically used for protecting group cleavage. Other "cassette"-based Fmoc solid phase peptide synthesis (SPPS) techniques potentially leading to glycopeptide thioesters also include acidic conditions at some point. These methods involve alteration of the Fmoc deblocking conditions [(a) Li, X. Q.; Kawakami, T.; Aimoto, S. *Tetrahedron Lett.* 1998, 39, 8669-8672; (b) Clippingdale, A. B.; Barrow, C. J.; Wade, J. D. *J. Pept. Sci.* 2000, 6, 225-234; (c) Hojo, H.; Haginoya, E.; Matsumoto, Y.; Nakahara, Y.; Nabeshima, K.; Toole, B. P.; Watanabe, Y. *Tetrahedron Lett.* 2003, 44, 2961-2964], or direct conversion into thioesters of C-terminal acids (von Eggelkraut-Gottanka, R.; Klose, A.; Beck-Sickinger, A. G.; Beyermann, M. *Tetrahedron Lett.* 2003, 44, 3551-3554), esters (Swinnen, D.; Hilvert, D. *Org. Lett.* 2000, 2, 2439-2442), or trithioorthoesters (Brask, J.; Albericio, F.; Jensen, K. J. *Org. Lett.* 2003, 5, 2951-2953). Boc-based SPPS employs strongly acidic cleavage conditions (liquid HF) that are incompatible with many glycosidic linkages.

(17) See: Verhaeghe, J.; Lacassie, E.; Bertrand, M.; Trudelle, Y. *Tetrahedron Lett.* 1993, 34, 461-464, and references therein.

(18) Caserio, M. C.; Fisher, C. L.; Kim, J. K. *J. Org Chem.* 1985, 50, 4390-4393.

(19) The protected peptide acid was synthesized by Fmoc SPPS.

(20) The aryl ester functional group is not intended for use in Fmoc SPPS; the design and synthesis of analogs appropriate for SPPS is currently underway, and will be reported in due course.

(21) Glycopeptide 18 was prepared as described previously (ref. 13).

(22) O-Linked glycopeptide precursors to 20 and 21 were synthesized using a cassette approach, in which the Fmoc serine monomers used in SPPS contained pendant saccharides.

(23) Kemp, D. S. In *The Peptides: Analysis, Synthesis, Biology*; Gross, E., Meienhofer, J., Eds.; Academic Press: New York, 1979; Vol. 1, Part A, pp 315-381.

(24) Shaltiel, S.; Fridkin, M. *Biochemistry* 1970, 9, 5122-5127.

(25) Wang, Z. G.; Zhang, X. F.; Live, D.; Danishefsky, S. J. *Angew. Chem. Int. Ed.* 2000, 39, 3652-3656.

(26) X. T. Chen, D. Sames, S. J. Danishefsky, *J. Am. Chem. Soc.* 1998, 120, 7760-7769.

(27) N. Bezay, G. Dudziak, A. Liese, H. Kunz, *Angew. Chem. Int. Ed.* 2001, 40, 2292-2295.

(28) J. van Ameijde, H. B. Albada, R. M. J. Liskamp, *J. Chem. Soc.-Perkin Trans.* 1 2002, 1042-1049.

(29) M. Ciommer, H. Kunz, *Synlett* 1991, 593-595.

(30) M. V. Chiesa, R. R. Schmidt, Eur. *J. Org. Chem.* 2000, 3541-3554.

(31) E. Meinjohanns, M. Meldal, K. Bock, *Tetrahedron Lett.* 1995, 36, 9205-9208.

(32) C. Unverzagt, *Tetrahedron Lett.* 1997, 38, 5627-5630.

(33) K. Witte, P. Sears, R. Martin, C. H. Wong, *J. Am. Chem. Soc.* 1997, 119, 2114-2118.

(34) L. X. Wang, M. Tang, T. Suzuki, K. Kitajima, Y. Inoue, S. Inoue, J. Q. Fan, Y. C. Lee, *J. Am. Chem. Soc.* 1997, 119, 11137-11146.

(35) G. Arsequell, G. Valencia, *Tetrahedron: Asymmetry* 1999, 10, 3045-3094.

(36) M. Mizuno, K. Haneda, R. Iguchi, I. Muramoto, T. Kawakami, S. Aimoto, K. Yamamoto, T. Inazu, *J. Am. Chem. Soc.* 1999, 121, 284-290.

(37) K. M. Koeller, M. E. B. Smith, R. F. Huang, C. H. Wong, *J. Am. Chem. Soc.* 2000, 122, 4241-4242.

(38) O. Blixt, K. Allin, L. Pereira, A. Datta, J. C. Paulson, *J. Am. Chem. Soc.* 2002, 124, 5739-5746.

(39) S. T. Anisfeld, P. T. Lansbury, *J. Org. Chem.* 1990, 55, 5560-5562.

(40) S. T. Cohen-Anisfeld, P. T. Lansbury, *J. Am. Chem. Soc.* 1993, 115, 10531-10537.

(41) E. Meinjohanns, M. Meldal, H. Paulsen, R. A. Dwek, K. Bock, *J. Chem. Soc.-Perkin Trans.* 1 1998, 549-560.

(42) P. E. Dawson, T. W. Muir, I. Clark-Lewis, S. B. H. Kent, *Science* 1994, 266, 776-779.

(43) C. F. Liu, J. P. Tam, *Proc. Natl. Acad. Sci. U.S.A.* 1994, 91, 6584-6588.

(44) T. W. Muir, D. Sondhi, P. A. Cole, *Proc. Natl. Acad Sci. U.S.A.* 1998, 95, 6705-6710.

(45) D. Macmillan, C. R. Bertozzi, Tetrahedron 2000, 56, 9515-9525.

(46) T. J. Tolbert, C. H. Wong, *J. Am. Chem. Soc.* 2000, 122, 5421-5428.

(47) Y. Shin, K. A. Winans, B. J. Backes, S. B. H. Kent, J. A. Eliman, C. R. Bertozzi, *J. Am. Chem. Soc.* 1999, 121, 11684-11689.

(48) a) Dawson, P. E.; Muir, T. W.; Clark-Lewis, I.; Kent, S. B. H. *Science* 1994, 266, 776. b) Dawson, P. E.; Kent, S. B. H. *Annu. Rev. Biochem.* 2000, 69, 923. c) Grogan, M. J.; Pratt, M. R.; Marcaurelle, L. A.; Bertozzi, C. R. *Annu. Rev. Biochem.* 2002, 71, 593.

(49) a) Miller, J. S.; Dudkin, V. Y.; Lyon, G. J.; Muir, T. W.; Danishefsky, S. J. *Angew. Chem. Int. Ed.* 2003 42, 431. b) Dudkin, V. Y.; Miller, J. S.; Danishefsky, S. J. *J. Am. Chem. Soc.* Submitted for publication.

(50) Shin, Y.; Winans, K. A.; Backes, B. J.; Kent, S. B. H.; Ellman, J. A.; Bertozzi, C. R. *J. Am. Chem. Soc.* 1999, 121, 11684.

(51) There is an intermediate step in NCL during which there is a second transthio-esterification with MESNa. In our reactions we have never observed the free sulfhydryl of the phenyl ester. Rather complete conversion of the N-terminal to the corresponding MESNa thioester is observed within 3 min.

What is claimed is:

1. A method for preparing a peptide comprising a peptidic backbone made up of four or more amino acids;
wherein the method comprises a step of:
reacting a peptide acyl donor comprising a peptidic backbone made up of two or more amino acids wherein said peptide acyl donor has the structure:

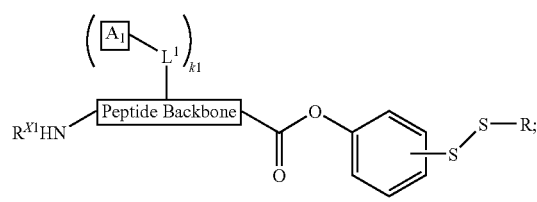

with a peptide amine acceptor having the structure:

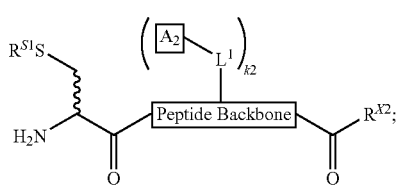

under reducing reaction conditions employing an excess of a reducing agent;
wherein k1 and k2 are independently integers between 1 and about 20;
each occurrence of $A_1$ and $A_2$ is independently an aliphatic, heteroaliphatic, aromatic, heteroaromatic, aryl, heteroaryl group;
$R^{S1}$ is a sulfide protecting group;
R is aliphatic, heteroaliphatic, aromatic or heteroaromatic;
each occurrence of $L^1$ is independently substituted or unsubstituted, linear or branched, cyclic or acyclic, saturated or unsaturated aliphatic or heteroaliphatic;

$R^{X1}$ is hydrogen, alkyl, acyl, aromatic, heteroaromatic, aryl, heteroaryl, -alkyl(aryl), -alkyl(heteroaryl), a nitrogen protecting group, an amino acid or a proctected amino acid; and $R^{X2}$ is —$OR^{X2a}$ or —$NR^{X2b}R^{X2c}$, wherein $R^{X2a}$ is hydrogen, alkyl, aromatic, heteroaromatic, aryl, heteroaryl, -alkyl(aryl), -alkyl(heteroaryl), a carboxylic acid protecting group, an amino acid or a proctected amino acid; and $R^{X2b}$ and $R^{X2c}$ are independently hydrogen, alkyl, aromatic, heteroaromatic, aryl, heteroaryl, -alkyl(aryl), -alkyl(heteroaryl), a nitrogen protecting group, an amino acid or a proctected amino acid.

2. The method of claim 1, wherein each occurrence of $A_1$ and $A_2$ is independently a carbohydrate determinant, a small molecule, or a diagnostic label.

3. The method of claim 1, wherein each occurrence of $A_1$ and $A_2$ is independently a carbohydrate determinant having the structure:

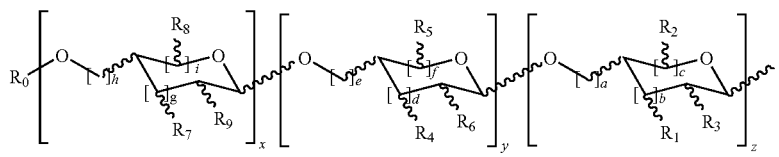

wherein a, b, c, d, e, f, g, h, i, x, y and z are independently 0, 1, 2 or 3, with the proviso that the x, y and z bracketed structures represent furanose or pyranose groups and the sum of b and c is 1 or 2, the sum of d and f is 1 or 2, and the sum of g and i is 1 or 2, and with the proviso that x, y and z are not simultaneously 0; wherein $R_0$ is hydrogen, a linear or branched chain alkyl, acyl, arylalkyl or aryl group; wherein each occurrence of $R_1$, $R_2$, $R_3$, $R_4$, $R_5$, $R_6$, $R_7$, $R_8$ and $R_9$ is independently hydrogen, OH, $OR^i$, $NHR^i$, $NHCOR^i$, F, $CH_2OH$, $CH_2OR^i$, a substituted or unsubstituted linear or branched chain alkyl, (mono-, di- or tri)hydroxyalkyl, (mono-, di- or tri)acyloxyalkyl, arylalkyl or aryl group; wherein each occurrence of $R^i$ is independently hydrogen, CHO, $COOR^{ii}$, or a substituted or unsubstituted linear or branched chain alkyl, acyl, arylalkyl or aryl group or a saccharide having the structure:

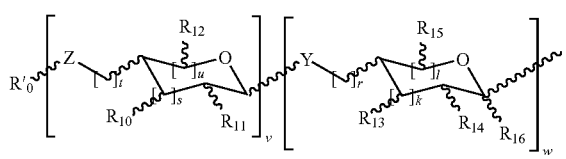

wherein Y and Z are independently NH or O; wherein k, l, r, s, t, u, v and w are each independently 0, 1 or 2; with the proviso that the v and w bracketed structures represent furanose or pyranose groups and the sum of l and k is 1 or 2, and the sum of s and u is 1 or 2, and with the proviso that v and w are not simultaneously 0; wherein $R'_0$ is hydrogen, a linear or branched chain alkyl, acyl, arylalkyl or aryl group; wherein each occurrence of $R_{10}$, $R_{11}$, $R_{12}$, $R_{13}$, $R_{14}$ and $R_{15}$ is independently hydrogen, OH, $OR^{iii}$, $NHR^{iii}$, $NHCOR^{iii}$, F, $CH_2OH$, $CH_2OR^{iii}$, or a substituted or unsubstituted linear or branched chain alkyl, (mono-, di- or tri)hydroxyalkyl, (mono-, di- or tri)acyloxyalkyl, arylalkyl or aryl group; wherein each occurrence of $R_{16}$ is hydrogen, COOH, $COOR^{ii}$, $CONHR^{ii}$, a substituted or unsubstituted linear or branched chain alkyl or aryl group; wherein each occurrence of $R^{iii}$ is hydrogen, CHO, $COOR^{iv}$, or a substituted or unsubstituted linear or branched chain alkyl, acyl, arylalkyl or aryl group; and wherein each occurrence of $R^{ii}$ and $R^{iv}$ are each independently H, or a substituted or unsubstituted linear or branched chain alkyl, arylalkyl or aryl group.

4. The method of claim 1, wherein each occurrence of $L^1$ is independently —O—$(CH_2)_n$—, wherein n is 0-9, or a glycoside-containing group.

5. The method of claim 1, wherein $L^1$ is —O—$(CH_2)_n$—$CH_2$— and two or more non-adjacent amino acids is/are independently substituted with a group having the structure:

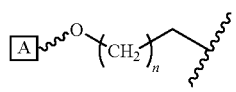

wherein each occurrence of n is independently 0-8.

6. The method of claim 1, wherein each occurrence of $A_1$ and $A_2$ is independently selected from the group consisting of Globo-H, fucosyl GM1, KH-1, glycophorin, STn, (2,3)ST, $Le^y$, $Le^x$, N3, Tn, 2,6-ST, Gb3 and TF.

7. The method of claim 1, wherein the peptide has the structure:

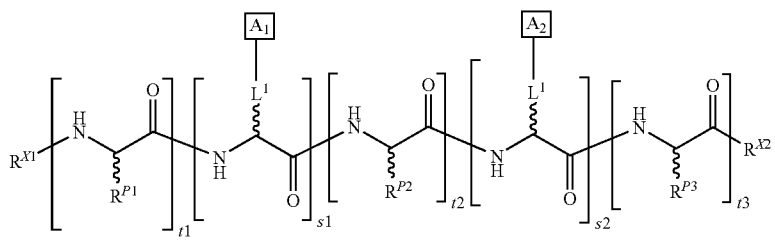

wherein s1 and s2 are independently an integer from 1 to about 20;

t1, t2 and t3 are each independently an integer;

$R^{X1}$ is hydrogen, alkyl, acyl, aromatic, heteroaromatic, aryl, heteroaryl, -alkyl(aryl), -alkyl(heteroaryl), a nitrogen protecting group, an amino acid or a proctected amino acid;

$R^{X2}$ is —$OR^{X2a}$ or —$NR^{X2b}R^{X2c}$, wherein $R^{X2a}$ is hydrogen, alkyl, aromatic, heteroaromatic, aryl, heteroaryl, -alkyl(aryl), -alkyl(heteroaryl), a carboxylic acid protecting group, an amino acid or a proctected amino acid; and $R^{X2b}$ and $R^{X2c}$ are independently hydrogen, alkyl, aromatic, heteroaromatic, aryl, heteroaryl, -alkyl(aryl), -alkyl(heteroaryl), a nitrogen protecting group, an amino acid or a proctected amino acid;

$R^{P1}$, $R^{P2}$ and $R^{P3}$ are independently H, alkyl, heteroalkyl, aromatic, heteroaromatic, aryl, heteroaryl, -alkyl(aryl), -alkyl(heteroaryl), or a natural or non-natural amino acid side chain;

each occurrence of $L^1$ is independently substituted or unsubstituted aliphatic or heteroaliphatic;

$A_1$ and $A_2$ are each independently an aliphatic, heteroaliphatic, aromatic, heteroaromatic, aryl, heteroaryl group; and at least one occurrence of the bracketed structure t2 is a cysteine residue or protected cysteine residue;

and the method comprises a step of:

reacting a peptide acyl donor having the structure:

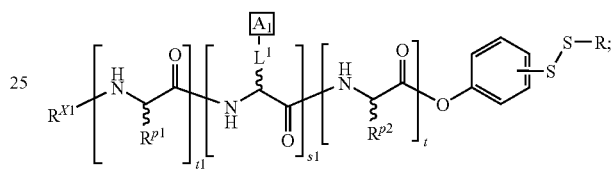

with a peptide amine acceptor having the structure:

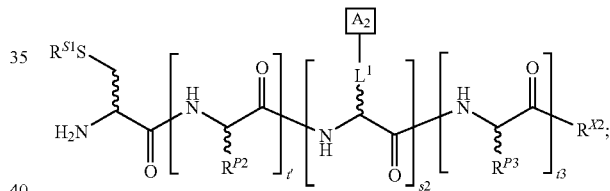

under suitable reaction conditions employing an excess of a reducing agent;

wherein the sum t+t' equals (t2)+1.

8. The method of claim 7, wherein the step of reacting the peptide acyl donor with the peptide amine acceptor is repeated a desired number of times, to prepare a peptide having the structure:

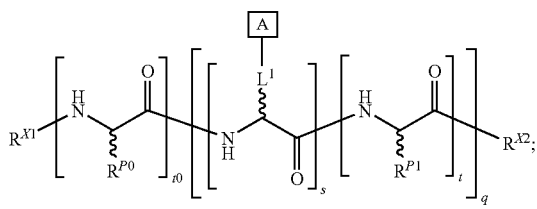

wherein $R^{X1}$ and $R^{X2}$ are as defined in claim 7;
each occurrence of A may be the same or different and may be as defined for $A_1$ and $A_2$ in claim 7;
each occurrence of $R^{P1}$ may be the same or different and may be as defined for $R^{P1}$ and $R^{P2}$ in claim 7;
q is an integer greater than or equal to 2;
each occurrence of s is independently an integer from 1 to about 20;
each occurrence of t is independently an integer;
t0 is an integer; and
each occurrence of $R^{P0}$ is independently H, alkyl, heteroalkyl, aromatic, heteroaromatic, aryl, heteroaryl, -alkyl(aryl), -alkyl(heteroaryl), or a natural or non-natural amino acid side chain.

9. The method of claim 8, wherein q is an integer between 2 and about 5.

10. The method of claim 8, wherein q is 2.

11. The method of claim 8, wherein the sum s+t is between about 2 and about 6.

12. The method of claim 8, wherein t0 is an integer from 0 to about 20.

13. The method of claim 8, wherein $R^{X1}$ is hydrogen, Fmoc or Ac.

14. The method of claim 8, wherein $R^{X2}$ is $NH_2$.

15. The method of claim 1, wherein the peptide acyl donor has the structure:

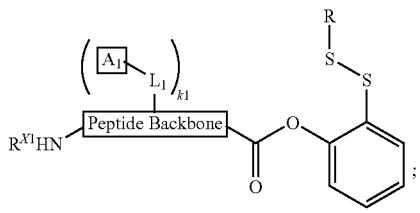

wherein R is lower alkyl.

16. The method of claim 15, wherein R is ethyl.

17. The method of claim 8, wherein $R^{S1}$ is —StBu.

18. The method of claim 8, wherein in the step of reacting the peptide acyl donor having the structure:

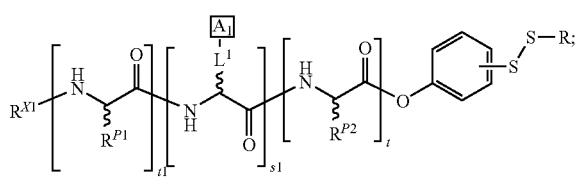

with the peptide amine acceptor, an intermediate having the following structure is formed in situ:

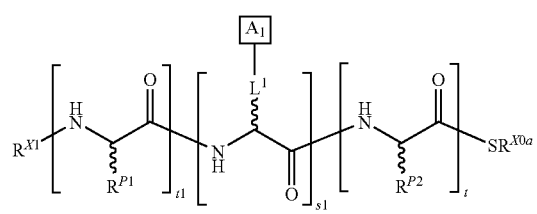

wherein $R^{X0a}$ is oxygen-substituted aryl.

19. The method of claim 18, wherein the reducing agent is 2-mercaptoethanesulfonic acid, sodium salt.

20. The method of claim 8, wherein in the peptide acyl donor has the structure:

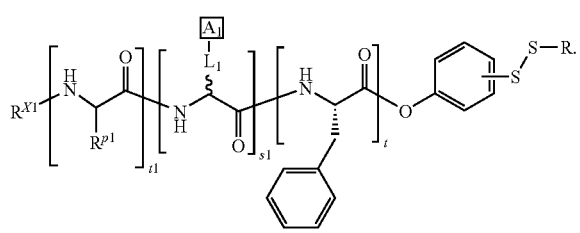

21. The method of claim 1, wherein at least one occurrence of $A_1$ or $A_2$, is a carbohydrate domain, and some or all of carbohydrate domains are O-linked to the peptide backbone.

22. The method of claim 1, wherein when at least one occurrence of $A_1$ or $A_2$, is a carbohydrate domain, and some or all of carbohydrate domains are N-linked to the peptide backbone.

23. The method of claim 1, wherein the peptide is symmetrical.

24. The method of claim 1, wherein the peptide is nonsymmetrical.

25. The method of claim 1, further comprising a step of conjugating the peptide to an immunogenic carrier.

26. The method of claim 25, wherein the carrier is a protein, a peptide or a lipid.

27. The method of claim 25, wherein the carrier is Bovine Serum Albumin (BSA), Keyhole Limpet Hemocyanin (KLH) or polylysine.

28. The method of claim 25, wherein the carrier is a lipid carrier having the structure:

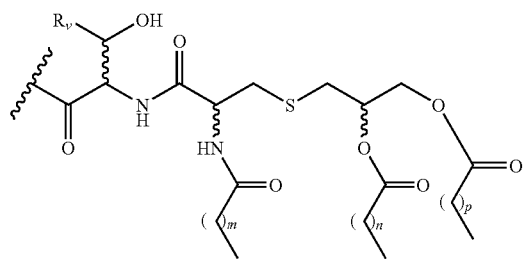

wherein m, n and p are each independently integers between about 8 and 20; and $R_v$ is hydrogen, substituted or unsubstituted linear or branched chain lower alkyl or substituted or unsubstituted phenyl.

29. The method of claim 28, wherein m', n' and p' are each 14.

30. The method of claim 25, wherein the carrier is linked to the peptide through a crosslinker.

31. The method of claim 30, wherein the crosslinker is a fragment having the structure:

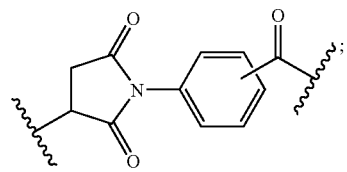

whereby said structure is generated upon conjugation of a maleimidobenzoic acid N-hydroxy succinimide ester with a suitable functionality on the peptide.

32. The method of claim 1, wherein the peptide has the structure:

(SEQ ID NO: 6)

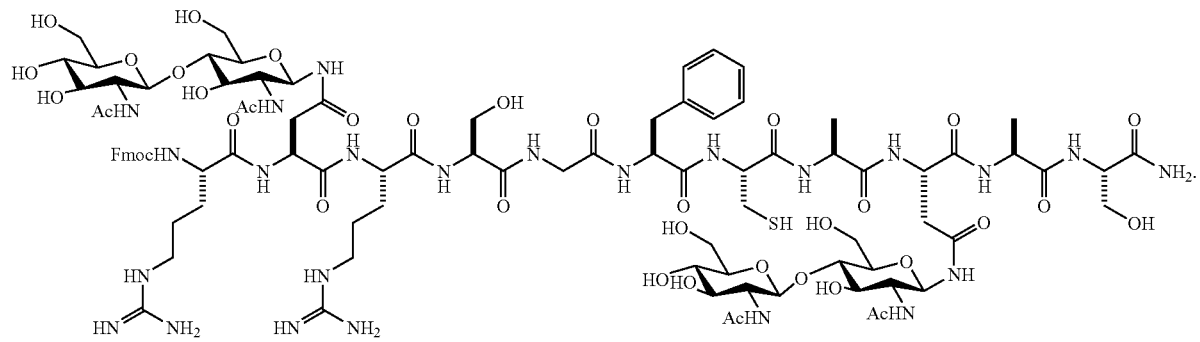

33. The method of claim 1, wherein the peptide has the structure:

(SEQ ID NO: 6)

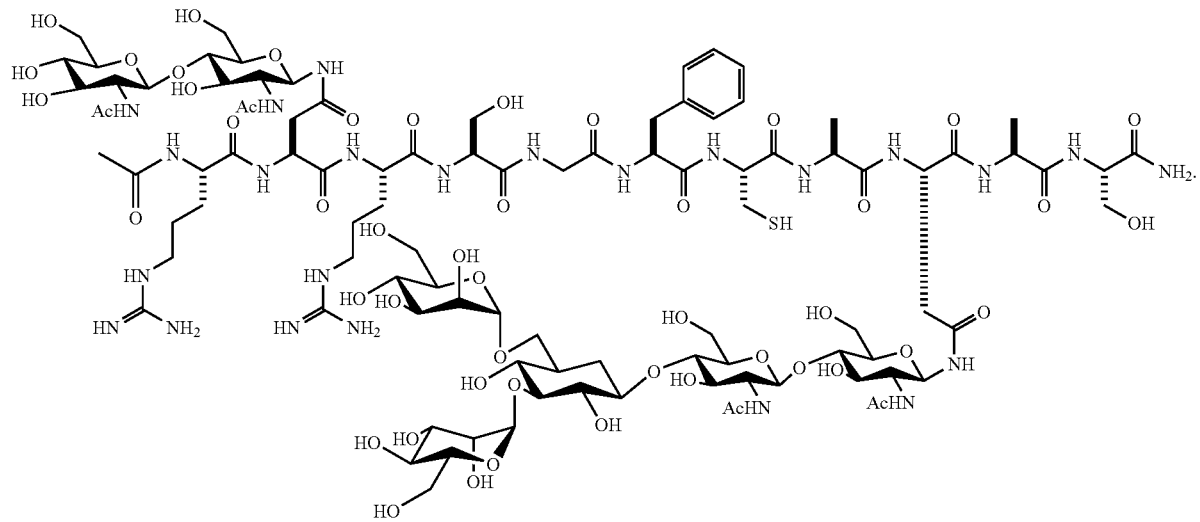

34. The method of claim 1, wherein the peptide has the structure:
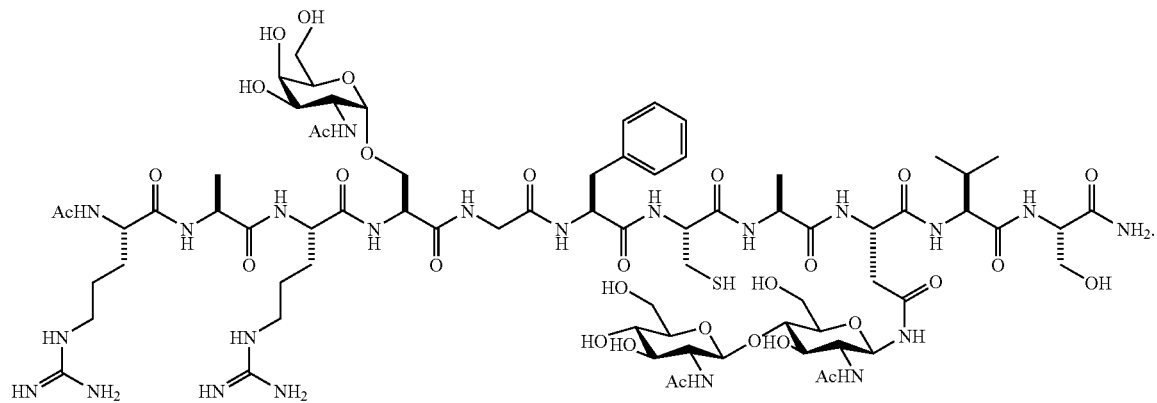
(SEQ ID NO: 7)
35. The method of claim 1, wherein the peptide has the structure:
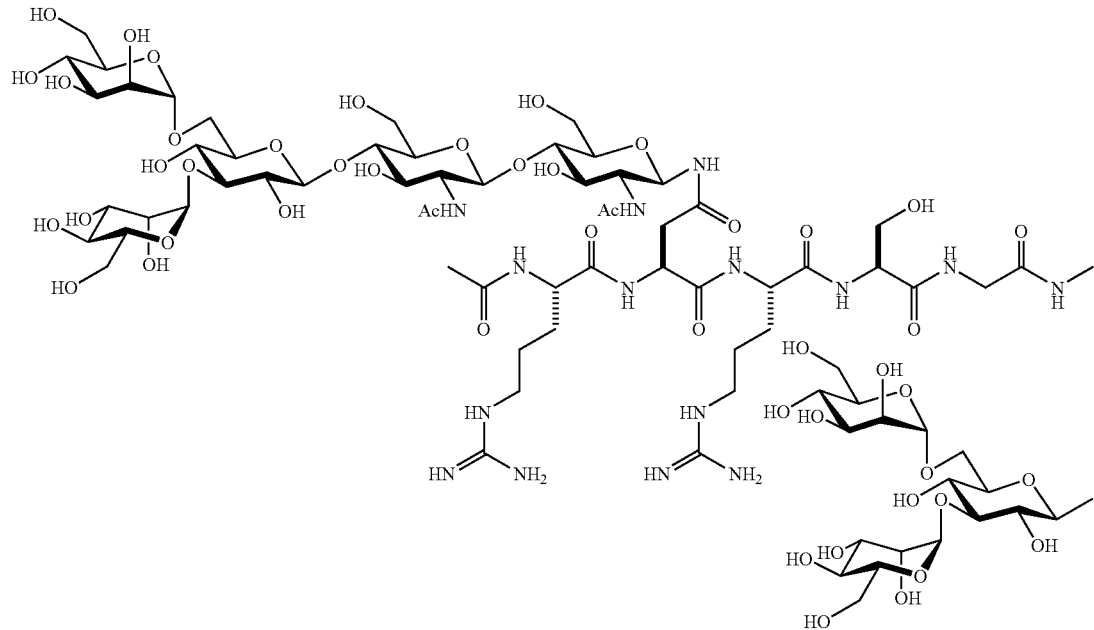
(SEQ ID NO: 6)

-continued
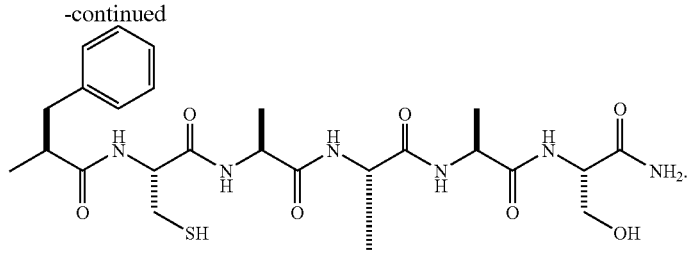
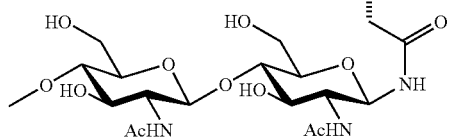
36. The method of claim 1, wherein the peptide has the structure:
(SEQ ID NO: 8)
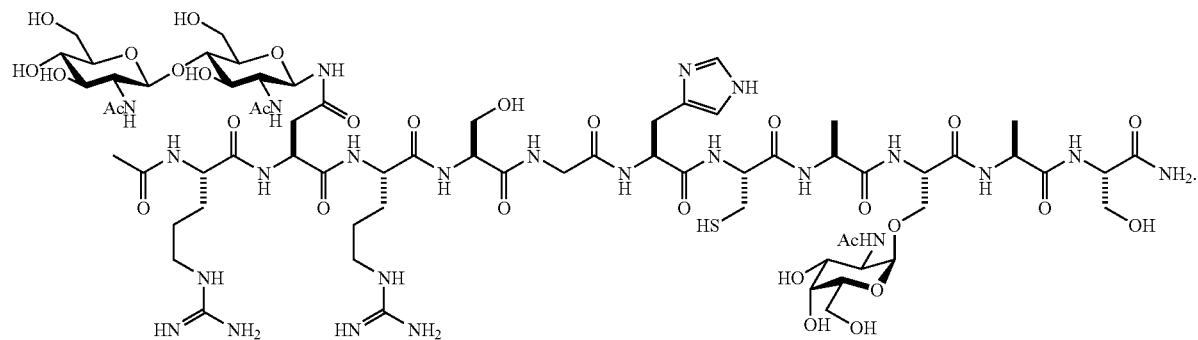
* * * * *

UNITED STATES PATENT AND TRADEMARK OFFICE
CERTIFICATE OF CORRECTION

PATENT NO.       : 7,635,750 B2
APPLICATION NO. : 10/570556
DATED            : December 22, 2009
INVENTOR(S)      : Danishefsky et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 414 days.

Signed and Sealed this

Ninth Day of November, 2010

David J. Kappos
*Director of the United States Patent and Trademark Office*

UNITED STATES PATENT AND TRADEMARK OFFICE
CERTIFICATE OF CORRECTION

| | | |
|---|---|---|
| PATENT NO. | : 7,635,750 B2 | Page 1 of 1 |
| APPLICATION NO. | : 10/570556 | |
| DATED | : December 22, 2009 | |
| INVENTOR(S) | : Samuel J Danishefsky | |

It is certified that error appears in the above-identified patent and that said Letters Patent is hereby corrected as shown below:

Specification

In column 1, beginning at line 17 and ending at line 22, please delete:

"The invention was made with U.S. government support under grants CA103823 (formerly AI16943), T32-CA62948, and AI051883 awarded by the National Institutes of Health. The U.S. government has certain rights in this invention."

and insert:

--This invention was made with government support under grant numbers AI051883, CA062948 and CA103823 awarded by The National Institutes of Health. The government has certain rights in the invention.--

Signed and Sealed this
Seventeenth Day of May, 2016

Michelle K. Lee
*Director of the United States Patent and Trademark Office*